(12) United States Patent
Baron et al.

(10) Patent No.: US 12,691,257 B2
(45) Date of Patent: Jul. 28, 2026

(54) INTRAVENOUS LINE HOLDER

(71) Applicant: IV-Glove Inc., Toronto (CA)

(72) Inventors: Manny Baron, Corunna (CA); Ross Harris, Corunna (CA); Kareem Sherif, Toronto (CA)

(73) Assignee: IV-Glove Inc., Toronto (CA)

( * ) Notice: Subject to any disclaimer, the term of this patent is extended or adjusted under 35 U.S.C. 154(b) by 668 days.

(21) Appl. No.: 18/001,750

(22) PCT Filed: Jun. 14, 2021

(86) PCT No.: PCT/CA2021/050808
§ 371 (c)(1),
(2) Date: Dec. 14, 2022

(87) PCT Pub. No.: WO2021/253114
PCT Pub. Date: Dec. 23, 2021

(65) Prior Publication Data
US 2023/0226319 A1 Jul. 20, 2023

Related U.S. Application Data

(60) Provisional application No. 63/039,128, filed on Jun. 15, 2020.

(51) Int. Cl.
*A61M 25/02* (2006.01)

(52) U.S. Cl.
CPC ..... *A61M 25/02* (2013.01); *A61M 2025/0213* (2013.01); *A61M 2025/024* (2013.01); *A61M 2025/028* (2013.01)

(58) Field of Classification Search
CPC ...... A61M 2025/028; A61M 2025/024; A61M 25/02; A61M 2025/0246
See application file for complete search history.

(56) References Cited

U.S. PATENT DOCUMENTS

| | | | |
|---|---|---|---|
| 5,116,324 A | 5/1992 | Brierley et al. | |
| 5,342,317 A | 8/1994 | Claywell | |
| 5,577,516 A | 11/1996 | Schaeffer | |
| 5,916,199 A | 6/1999 | Miles | |
| 6,572,588 B1 * | 6/2003 | Bierman | A61M 25/02 |
| | | | 604/174 |

(Continued)

FOREIGN PATENT DOCUMENTS

| | | |
|---|---|---|
| JP | 2009-254890 A | 11/2009 |
| KR | 10-1822793 B1 | 1/2018 |

(Continued)

OTHER PUBLICATIONS

International Search Report, Search Strategy and Written Opinion of record in WO2020124214, dated Jun. 25, 2020.

(Continued)

*Primary Examiner* — Courtney B Fredrickson
(74) *Attorney, Agent, or Firm* — Zeman-Mullen & Ford, LLP

(57) ABSTRACT

Described is an intravenous line housing defining an intravenous line guide. The intravenous line guide is configured to hold the intravenous line and direct the intravenous line along a path. Also provided is an apparatus comprising the intravenous housing and a securing means to secure the intravenous line housing to the patient.

5 Claims, 33 Drawing Sheets

(56)  References Cited

U.S. PATENT DOCUMENTS

| 8,123,681 | B2 | | 2/2012 | Schaeffer | |
|---|---|---|---|---|---|
| 2012/0216385 | A1 | * | 8/2012 | Taylor ................... | A61M 25/02 |
| | | | | | 428/156 |
| 2019/0388652 | A1 | | 12/2019 | Albany | |

FOREIGN PATENT DOCUMENTS

| TW | M542480 | U | 6/2017 |
|---|---|---|---|
| WO | 2020124214 | A1 | 6/2020 |

OTHER PUBLICATIONS

International Search Report, Search Strategy and Written Opinion of record in WO2021253114, dated Dec. 23, 2021.
JS U.S. Appl. No. 62/780,293, filed Dec. 16, 2018 as the priority document published with WO2020124214 on Jun. 25, 2020.

* cited by examiner

4130

4120

4000

4300

4200

4120

4110

4130

10600

3000

9710

23200

9720

23200

INTRAVENOUS LINE HOLDER

RELATED APPLICATIONS AND PRIORITY CLAIM

This application is the U.S. national phase (national stage entry) of International Application No. PCT/CA2021/050808 filed Jun. 14, 2021, which designates the U.S. and claims priority to U.S. Provisional Patent Application No. 63/039,128 filed Jun. 15, 2020, the entire contents of each of which are hereby incorporated by reference.

FIELD OF THE INVENTION

The present specification relates generally to medical devices, and specifically to an apparatus for holding an intravenous line.

BACKGROUND OF THE INVENTION

Intravenous lines are commonly used to introduce fluid into a patient. Intravenous lines often include an intravenous tube and an intravenous tip; the intravenous tube provided to carry a fluid from a source to the tip. The tip is commonly inserted through the skin of a patient and into a vein.

When the tip of an intravenous line is inserted through the skin it is often desirable to secure the line to the anatomy of the patient. Movement of the line can contribute to a variety of issues, such as removal of the tip from the vein or subcutaneous damage caused by movement of the tip.

A variety of fasteners have been employed to hold intravenous lines. For example, adhesive tape is commonly used to secure a line to a patient. Various straps and gloves have also been developed, many of which perform dual roles in securing an intravenous line and shielding the insertion point from contamination. However, these fasteners have many limitations, and none provide an ideal solution.

Accordingly, there remains a need for improvements in the art.

SUMMARY OF THE INVENTION

An object of the present invention is an intravenous line holder. In one aspect of the present invention, there is provided an intravenous line housing defining an intravenous line guide, the intravenous line guide configured to hold the intravenous line and direct the intravenous line along a path for entry into skin of a patient. In certain embodiments, the intravenous line housing includes a set of projections forming an at least one clip for holding the intravenous line as part of the intravenous line guide. In certain embodiments, the intravenous line guide is curved, optionally the curved intravenous line guide includes at least two curvatures, optionally the curved intravenous line guide is an s-clip guide.

In another aspect of the present invention, there is provided an apparatus for supporting an intravenous line comprising the intravenous line housing of the present invention and a securing means attached to the intravenous line housing, the structure configured to secure the intravenous line housing to the patient. In certain embodiments, the securing means is a glove secured to the intravenous line housing, the glove configured to hold the intravenous line housing to a user's hand. In certain embodiments, the securing means comprises a flexible strap structure. In certain embodiments, the securing means is a sleeve. In certain embodiments, the intravenous line guide comprises a recessed portion in the intravenous line housing.

In another aspect of the present invention, there is provided an apparatus for supporting an intravenous line, comprising: an intravenous line housing defining an intravenous line guide, the intravenous line guide configured to hold the intravenous line and direct the intravenous line along a reversing path and to a substantially proximally-directed entry angle for entry into a dorsal surface of a user's hand; and a glove secured to the intravenous line housing, the glove configured to hold the intravenous line housing to the user's hand. In certain embodiments, the glove comprises a flexible strap structure. In certain embodiments, the intravenous line guide comprises a recessed portion in the intravenous line housing. In certain embodiments, the intravenous line housing comprises at least four multi-way adjustable loops or eyelets. In certain embodiments, the multi-way adjustable loops or eyelets are three-way adjustable loops or eyelets. In certain embodiments, the at least four multi-way adjustable loops or eyelets are four three-way adjustable loops or eyelets. In certain embodiments, the flexible strap structure includes a mounting panel and a palm strap, the mounting panel configured to rest on the dorsal surface of the user's hand, the palm strap secured at a first end to a first side of the mounting panel, the palm strap configured to be wrapped around the palm of a user and releasably engaged at a second end to a second side of the mounting panel to hold the mounting panel against the dorsal surface of the user's hand. In certain embodiments, the apparatus further comprises a releasable fastener secured to one of the second end of the palm strap and second side of the mounting panel, the releasable fastener provided to permit the second end of the palm strap to be releasably engaged with the second side of the mounting panel. In certain embodiments, the releasable fastener is a ladder lock buckle. In certain embodiments, the flexible strap structure includes a finger loop for engaging a finger of the user's hand. In certain embodiments, the flexible strap structure is a continuous fabric panel. In certain embodiments, the intravenous line housing includes a set of projections forming an at least one clip for holding the intravenous line as part of the intravenous line guide. In certain embodiments, the intravenous line guide is curved, optionally the curved intravenous line guide includes at least two curvatures, optionally the curved intravenous line guide is an s-clip guide. In certain embodiments, the glove defines an access opening therethrough leaving a portion of the dorsal surface of the user's hand uncovered when the glove is worn, the intravenous line housing configured to direct the entry of the intravenous line into the user's hand through the access opening. In certain embodiments, the intravenous line housing includes a footing and an access opening cover, the footing secured to the glove and framing the access opening without covering the access opening, the access opening cover configured to be removably secured over the footing to cover the access opening. In certain embodiments, the access opening cover is clear to permit a user to view the dorsal surface of the user's hand through the access opening cover. In certain embodiments, the access opening cover rotates about a hinge to separate the access opening cover from the footing. In certain embodiments, the curved intravenous line guide is a mirrored s-clip guide. In certain embodiments, the intravenous line housing features at least one lateral aperture for receiving the intravenous line. In certain embodiments, the intravenous line housing features at least one ventilation aperture. In certain embodiments, the intravenous line housing features a splash guard.

In another aspect of the present invention, there is provided a glove for holding an intravenous line, comprising: a fabric panel configured to be releasably fastened to a user's hand; and a set of clips secured to the fabric panel, the set of clips configured to hold the intravenous line and direct the intravenous line along a reversing path and to a substantially proximally-directed entry into a dorsal surface of the user's hand. In certain embodiments, the fabric panel is a continuous panel which defines a clip mounting panel and a palm strap. In certain embodiments, the fabric panel further defines a finger loop for encircling the base of a finger of the user's hand. In certain embodiments, the glove further comprises an outer cover configured to cover the set of clips and to cover an entry point of the intravenous line. In certain embodiments, the set of clips are secured to the fabric panel by a set of fasteners, the set of fasteners adhered to the fabric panel and connected to the set of clips via an interference fit. In certain embodiments, the glove further comprises a releasable fastener secured to a first point on the fabric panel and provided for releasably engaging a second point on the fabric panel.

The intravenous line housing and apparatus of the invention may be used on any appropriate patient including for example, adult patients and pediatric patients including babies, children and teens. The intravenous line housing and apparatus of the invention may be used for veterinary patients.

Other aspects and features according to the present application will become apparent to those ordinarily skilled in the art upon review of the following description of embodiments of the invention in conjunction with the accompanying figures.

BRIEF DESCRIPTION OF THE DRAWINGS

The principles of the invention may better be understood with reference to the accompanying figures provided by way of illustration of an exemplary embodiment, or embodiments, incorporating principles and aspects of the present invention. The figures are not necessarily to scale and in some instances proportions may have been exaggerated in order more clearly to depict certain features of the invention.

FIG. 19a is a top plan view of an apparatus for holding an intravenous line according to an embodiment mounted on a user's hand and with an intravenous line affixed.

FIG. 19b is a top perspective view of the apparatus of FIG. 19a, removed from a user's hand.

FIG. 19c is a side view of the apparatus of FIG. 19a, without an intravenous line affixed.

FIG. 19d is a side view of the apparatus of FIG. 19a.

FIG. 19e is a side perspective view of the apparatus of FIG. 19a, removed from a user's hand.

FIG. 19f is a side perspective view of the apparatus of FIG. 19a, removed from a user's hand and showing a partially extended outer cover.

FIG. 19g is a side perspective view of the apparatus of FIG. 19a, removed from a user's hand and showing a fully extended outer cover.

FIG. 22b is a top plan view of the apparatus of FIG. 22a.

FIG. 22c is a front perspective view of the apparatus of FIG. 22a.

FIG. 22e is a side perspective view of the apparatus of FIG. 22a.

FIG. 22f is a close-up rear perspective view of the apparatus of FIG. 22a.

DETAILED DESCRIPTION OF THE INVENTION

Figure 1:
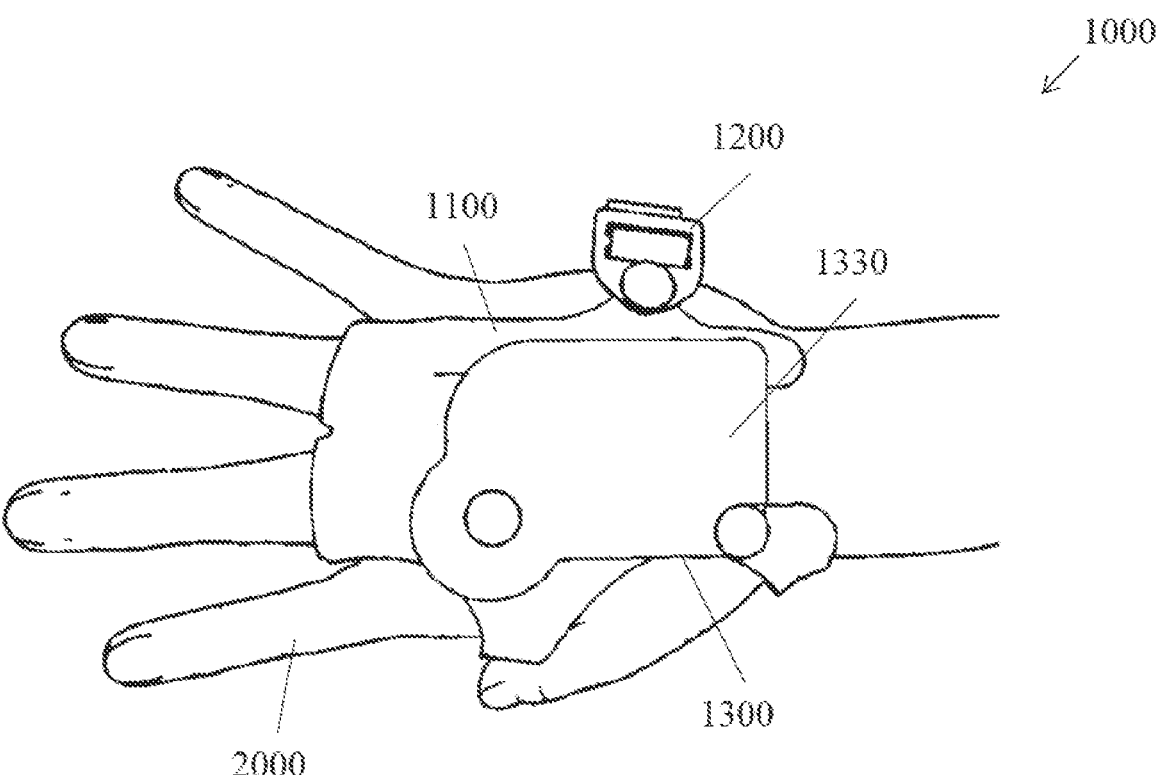
FIG. 1 is a top plan view of an apparatus for holding an intravenous line, according to an embodiment, mounted on a user's hand.

The present invention provides an intravenous line housing and an apparatus for supporting one or more intravenous lines comprising the intravenous line housing of the present invention and a securing means secured, either reversibly or irreversibly, to the intravenous line housing configured to secure the intravenous line housing to a patient.

The intravenous line housing may be constructed of various rigid material including but not limited to plastic. In certain embodiments, the housing is molded plastic. The housing may be of various sizes. For example, the housing may be sized to be mounted on a particular body part a hand, arm, leg, neck etc. In addition, the housing may be sized for adult or pediatric (including infants and children) patients.

The intravenous line housing is for supporting and guiding along a predetermined path one or more intravenous lines inserted into the skin of a patient. The intravenous line housing may also shield the insertion point or the intravenous line from contamination. In certain embodiments, the apparatus is for supporting and guiding one intravenous line. In other embodiments, the apparatus is for supporting and guiding two intravenous lines.

In certain embodiments, the intravenous line housing comprises one or more intravenous line guides each of which is designed to guide an intravenous line along a reversing path and to direct the intravenous line to a substantially proximally directed entry. In certain embodiments, the each of the one or more intravenous line guides is designed to guide each of the one or more intravenous lines along a curved path. The curved paths may be various shapes including but not limited to c-shaped, u-shaped, s-shaped and inverse s-shaped.

In certain embodiments, the housing comprises one or more intravenous line guides designed to guide one or more intravenous lines along a s-shaped and/or inverse s-shaped path. In certain embodiments, the housing comprises one intravenous line guide designed to guide one intravenous line along a s-shaped path and a second intravenous line guide designed to guide an intravenous line along an inverse s-shaped path. In some embodiments, more than one intravenous line passes through the apparatus and each intravenous line may be positioned differently within the apparatus, in order to accommodate right or left-handed users or various intravenous line insertion points.

The intravenous line guides may be in one or more various forms including but not limited to one or more projections from the housing, grooves in the housing and one or more straps.

In some embodiments, an intravenous line guide is a clip structure defined by a set of projections from the housing. In further embodiments, the intravenous line guide may be recessed into a groove in the housing and the intravenous line may be held by a friction fit. In certain embodiments, straps may be used to secure the intravenous line along a path. In certain embodiments, a combination of elements is used to secure an intravenous line along a path. For example, the intravenous line guide may be a groove in the housing or projections from the housing and one or more straps with accompanying snaps and eyelets are used to further secure the intravenous line.

In some embodiments, the intravenous line guide structure is a clip or a set of clips provided to hold an intravenous line in a predetermined position. In some embodiments, the intravenous line guide is a groove recessed into the housing provided to hold an intravenous line. In some embodiments, the intravenous line guide is a combination of a clip or set of clips and a cover or cap, which cooperate to hold an intravenous line in a predetermined position.

In certain embodiments, the housing may be covered with an outer cover. The outer cover may protect the portion of the intravenous line in the housing. In certain embodiments, the outer cover is removable. In other embodiments, the outer cover may be opened. In certain embodiments, the outer cover is a hinged outer cover that permits the opening and closing of an outer cover relative the housing. In certain embodiments, the outer cover is transparent and may function as an inspection dome. In certain embodiments, the outer cover is secured to the housing with one or more clips.

In certain embodiments, the intravenous line housing may be secured to the patient with adhesive tape.

In certain embodiments, a securing means is attached, reversibly or irreversibly, to the intravenous line housing. The securing means is configured to secure the intravenous line housing to a part of the patient's body, including for example a hand, foot, arm, leg or neck.

In certain embodiments, the securing means is a general securing means that can be used to secure the intravenous line housing to different body parts. In certain embodiments, the securing means is configured to secure the intravenous housing to specific types of body parts. In certain embodiments, the securing means is adjustable or configurable to the body part that the apparatus is to be secured to.

The securing means may include one or more straps, ties, sleeves, glove structures, sock structures or a combination thereof.

The securing means may be constructed from a rigid material such as hard plastic, flexible material, such as flexible plastic or a fabric or a combination thereof. In certain embodiments, the securing means further comprises one or more buckles, snaps, buttons or the like.

In certain embodiments, there is provided an apparatus comprising a glove structure and a housing defining an intravenous line guide (i.e. an intravenous line housing) and optionally a cover. In some embodiments, the glove structure is a rigid structure, including but not limited to a cast-style glove formed of rigid plastic or similar material. In some embodiments, the glove structure is semi-rigid, including but not limited to a glove formed of plastic plates coupled by flexible joints. In some embodiments, the glove structure is a flexible structure, such as a system of fabric straps.

In certain embodiments, there is provided an apparatus comprising a sleeve or band with closures and an intravenous line housing and optionally, a cover. In certain embodiments, the sleeve is a fabric or mesh like material.

In certain embodiments, there is provided an apparatus comprising straps and an intravenous line housing and optionally a cover. In certain embodiments, the straps comprise one or more buckles are fasteners.

In certain embodiments, there is provided a kit comprising an intravenous line housing and one or more securing means and optionally a cover.

Embodiments of the invention may be further described with reference to the figures.

An embodiment of an apparatus for holding an intravenous line is depicted in FIGS. 1 to 6. Apparatus 1000 includes a fabric glove 1100, a buckle 1200 and a housing 1300. Apparatus 1000 is shown secured to a hand 2000; the fabric glove 1100 is a continuous panel which is releasably secured via buckle 1200 to itself around hand 2000. Glove 1100 of apparatus 1000 forms a mounting panel 1110, a palm strap 1120, and a pair of finger loops 1130, shown particularly in FIGS. 3 and 4; mounting panel 1110 is provided to hold housing 1300, palm strap 1120 is provided to extend under the user's hand and join to the mounting panel 1110 via buckle 1200, and the forward finger loops 1130 are provided to fit over the fingers of a user.

Housing 1300 is provided to receive and hold a length of intravenous line, and to house the insertion point of an intravenous line into a dorsal surface of a user's hand. Housing 1300 is mounted on mounting panel 1110 of glove 1100 and configured to cover a portion of the dorsal surface of the user's hand.

Housing 1300 includes a footing 1310 secured to glove 1100 by a set of fasteners 1320. Housing 1300 also includes an outer cover 1330 secured to the footing 1310 by way of a combination of a friction overlay of footing 1310 and a set of fasteners 1350. Footing 1310 defines a set of clip projections 1340, together the set of clip projections 1340 define an intravenous line guide for holding an intravenous line. The outer cover 1330 also cooperates with the set of clip projections 1340 to hold the intravenous line in a predefined position. In some embodiments, a cover is a ventilated cover.

Figure 2:
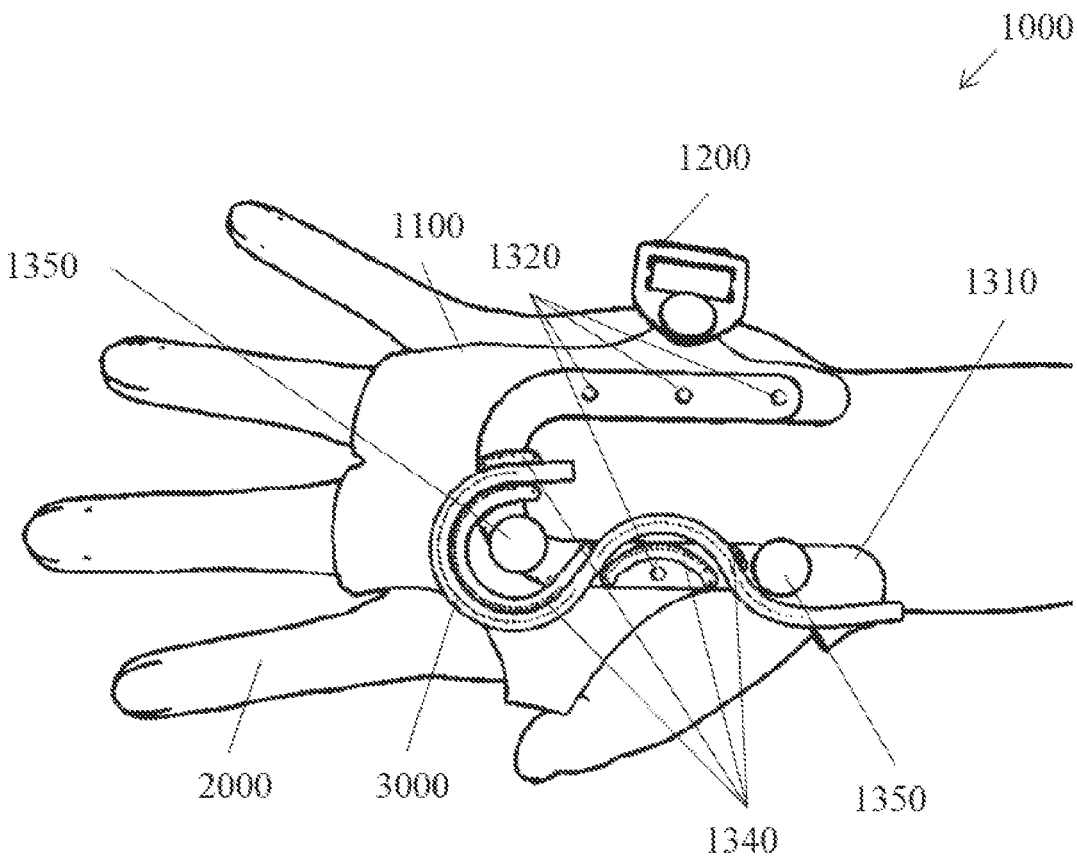
FIG. 2 is a top plan view of the apparatus of FIG. 1, mounted on a user's hand and with the outer cover removed and with an intravenous line affixed.
Figure 3:
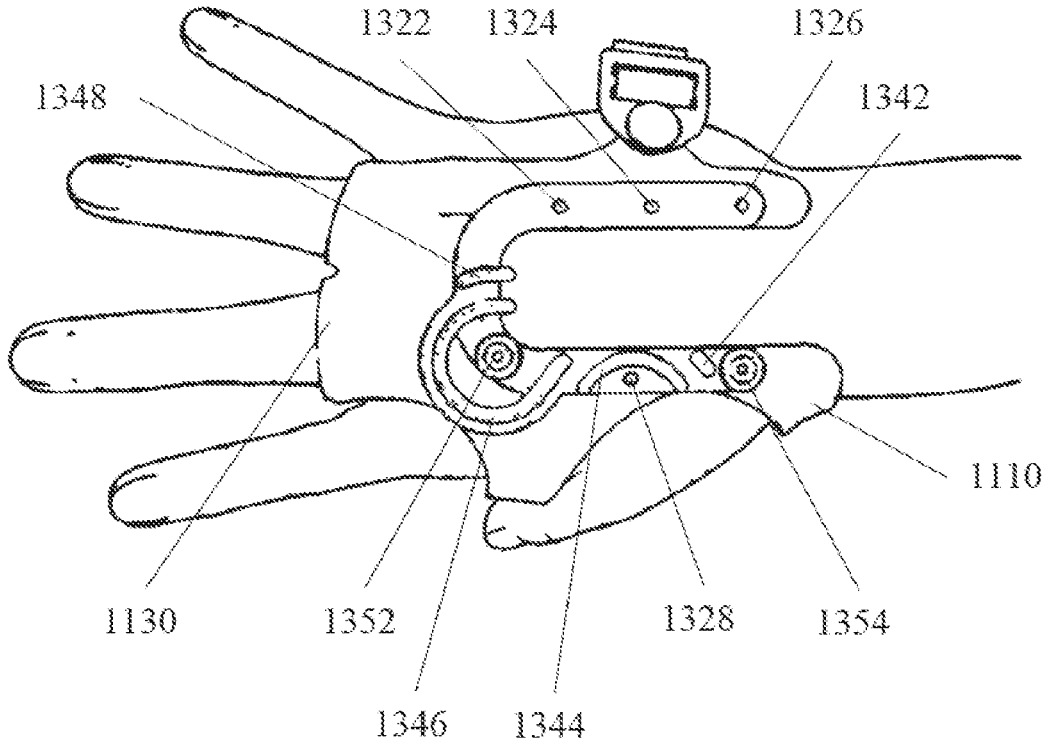
FIG. 3 is a top plan view of the apparatus of FIG. 1, mounted on a user's hand and with the outer cover removed.
Figure 4:
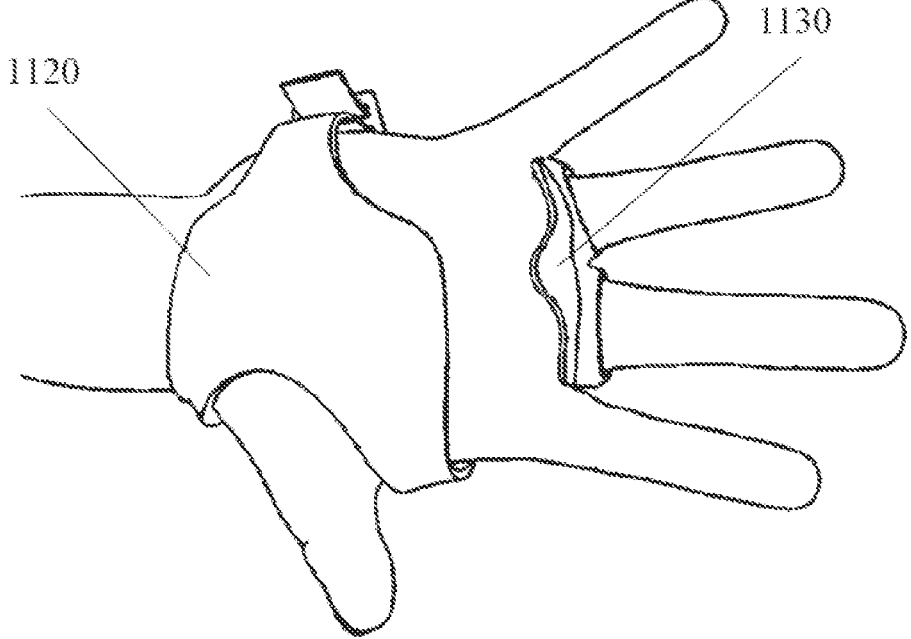
FIG. 4 is a bottom plan view of the apparatus of FIG. 1, mounted on a user's hand.
Figure 5:
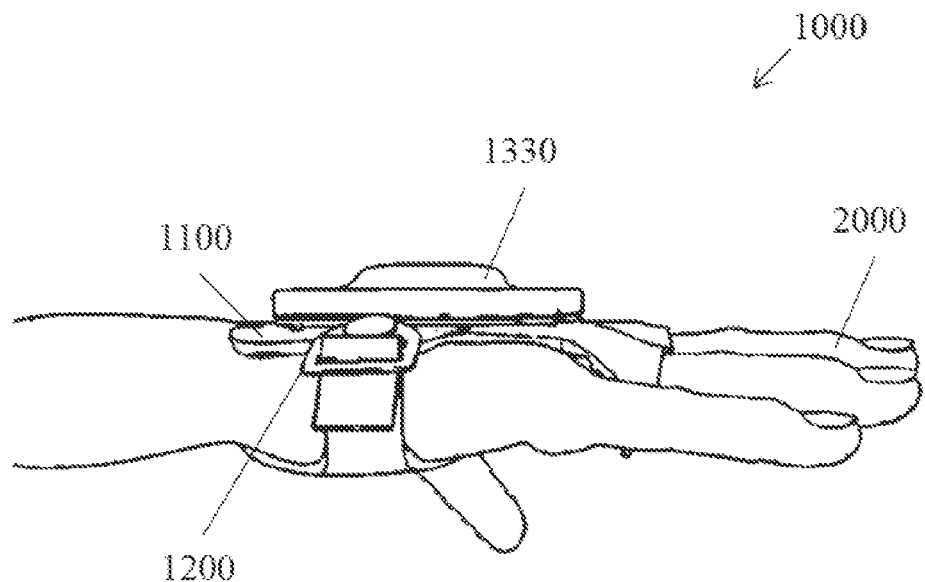
FIG. 5 is an elevation view of the apparatus of FIG. 1, mounted on a user's hand (5th digit side).
Figure 6:
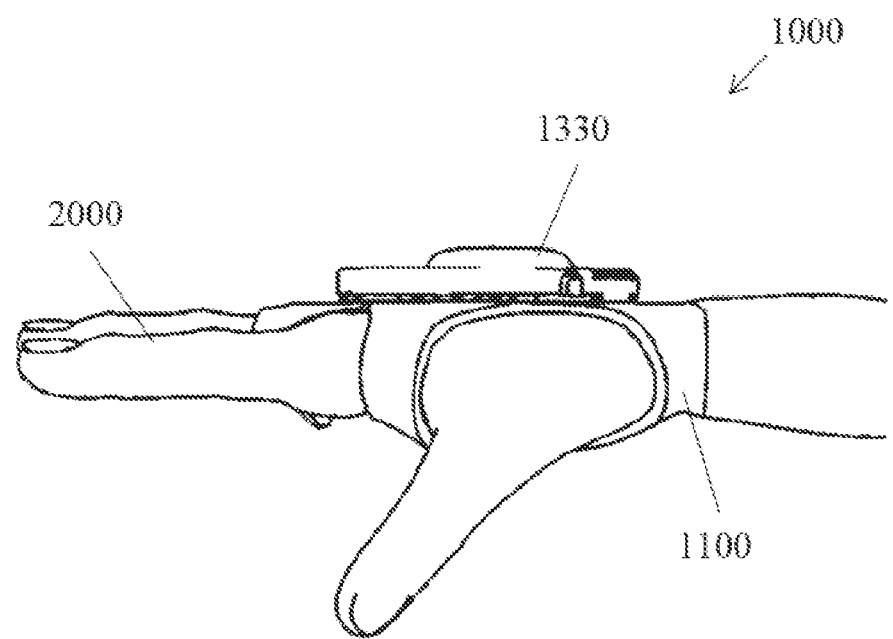
FIG. 6 is a side elevation view of the apparatus of FIG. 1, mounted on a user's hand (thumb side).

Apparatus 1000 is shown in FIG. 1 with outer cover 1330 of housing 1300 affixed. Apparatus 1000 is shown in FIGS. 2 and 3 with outer cover 1330 removed.

The set of clip projections 1340 of apparatus 1000 is a set of four projections. A first projection 1342 and a second projection 1344 define a beginning of an intravenous tube guide while a third projection 1346 and a fourth projection 1348 define an end of the intravenous tube guide.

Fasteners 1320 are a set of four pins, three on the right side 1322, 1324, and 1326 and one on the left 1328, bonded or adhered to glove 1100 and holding footing 1310 via an interference fit. Fasteners 1350 are a set of two pins, a distal pin 1352 and a proximal pin 1354, bonded or adhered to glove 1100 and designed so that cover 1330 may be received between a base portion of each pin and a cap portion, with the base and cap portions held to one another via an interference fit. While the embodiment shown uses an interference fit, in various embodiments the apparatus may have components secured to one another in a variety of ways, such as direct stitching, adhesion, hook-and-loop fasteners, and moulding. Glove 1100 of apparatus 1000 defines a dorsal opening which is provided to leave the back of a user's hand uncovered by glove 1100 in an area where an intravenous line is likely to be entered into the hand. Footing 1310 likewise defines a dorsal opening to leave the back of a user's hand uncovered. The dorsal opening is then covered by cover 1330 which sits over footing 1310 and the intravenous line guide defined by projections 1340. Cover 1330 is clear so that an entry site of the intravenous line 3000 may be observed, such as by a user or healthcare provider, without removing the cover 1330.

The use of a clear cover also allows for the observation of the part of the intravenous tube which is covered by the cover. Cover 1330 cooperates with the set of projections 1340, particularly projection 1346, to hold the intravenous line 3000 in position. Cover 1330 also includes a notch or opening to permit the entry of the intravenous line 3000 into the housing. Housing 1300 is configured to receive the intravenous line 3000 from a left side of the housing guide it along an s-shaped and reversing path, and direct it to a substantially proximally directed entry angle.

Housing 1300 defines an intravenous line guide using a combination of the clip projections 1340 and the cover 1330. As depicted, the intravenous line guide is an 's-clip' which defines an exaggerated s-shaped guide; accepting an intravenous line from a left side of the housing, guiding it around a first curve and then a reversing second curve to an entry point.

Figure 7:
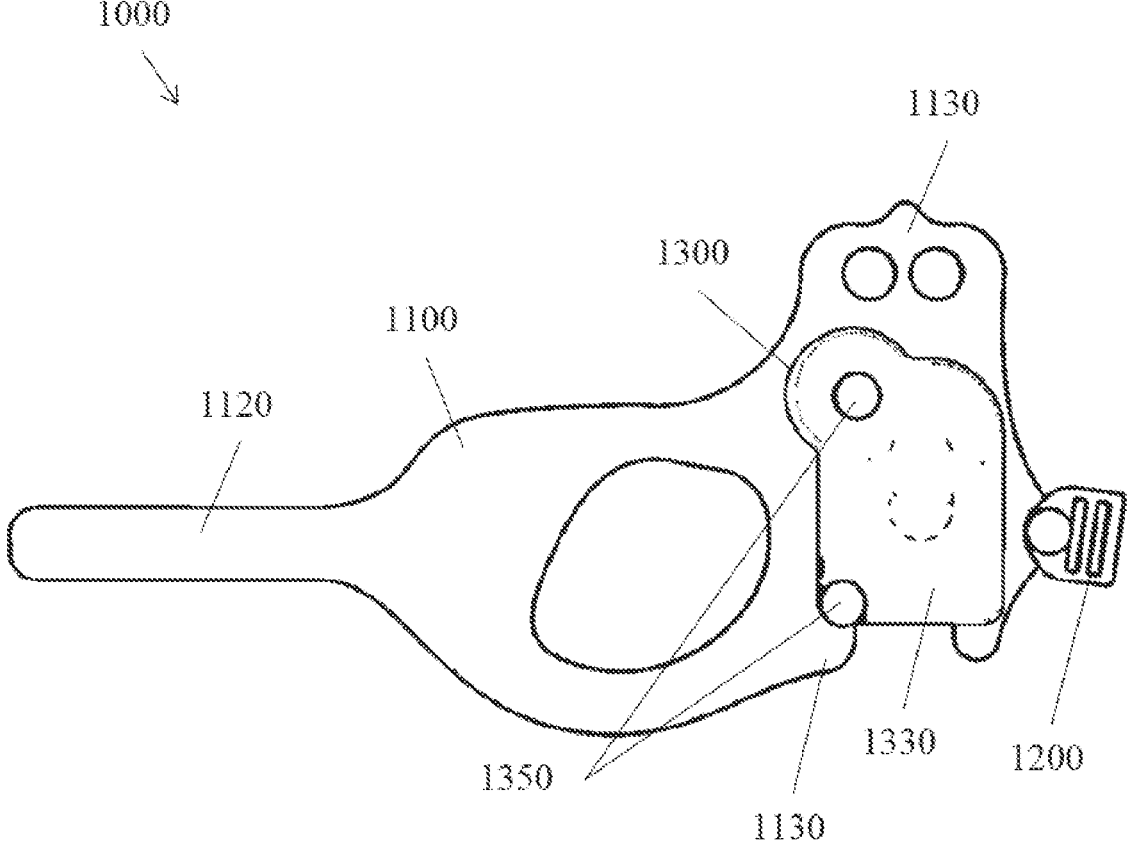
FIG. 7 is a top plan view of the apparatus of FIG. 1, opened and with the outer cover affixed.
Figure 8:
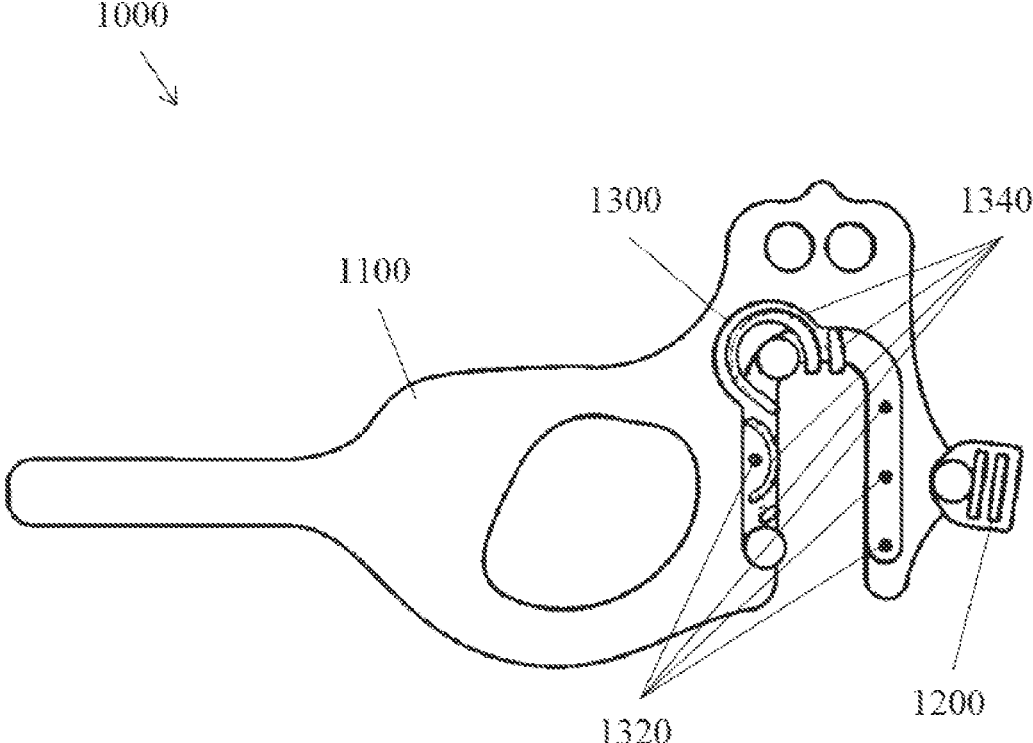
FIG. 8 is a top plan view of the apparatus of FIG. 1, opened and with the outer cover removed.
Figure 9:
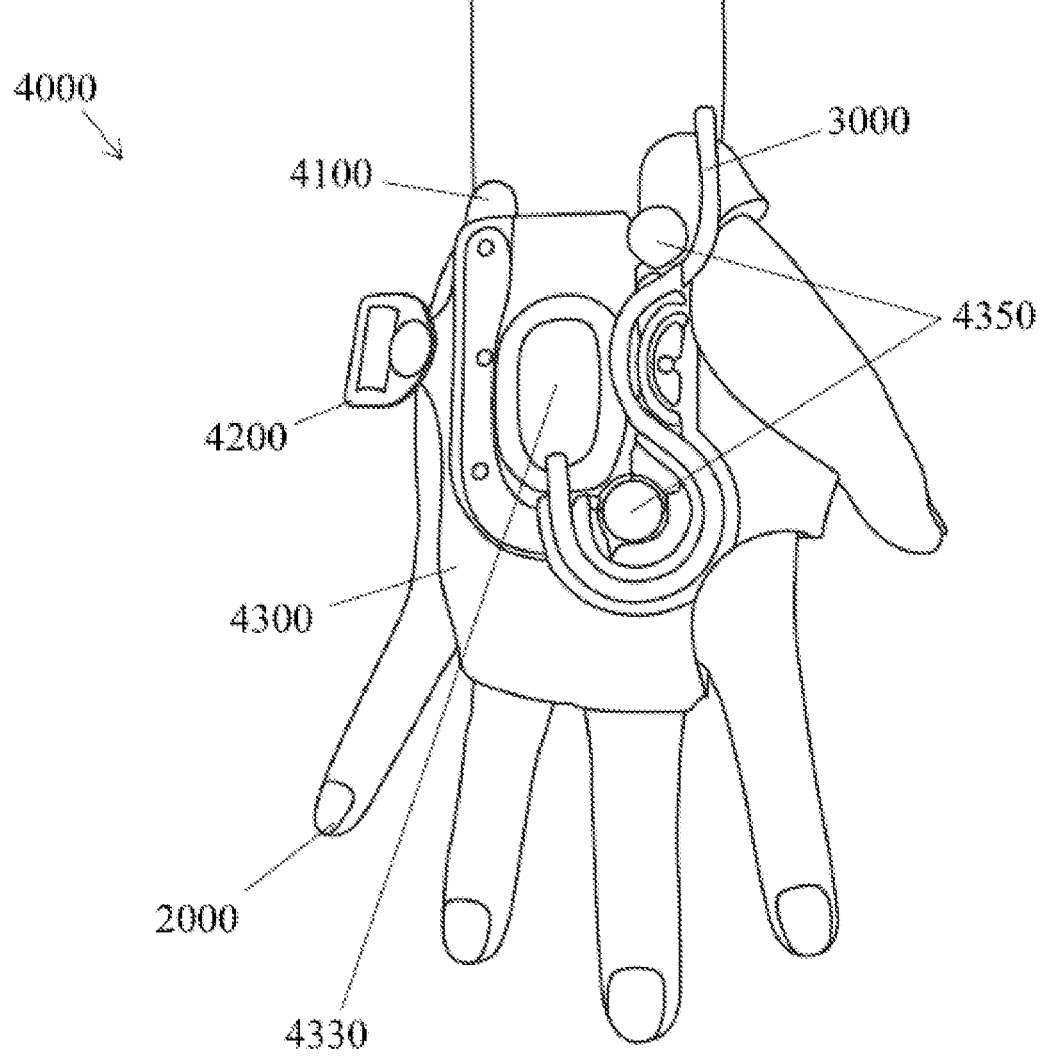
FIG. 9 is a top plan view of an apparatus for holding an intravenous line, according to an embodiment, mounted on a user's hand and with an intravenous line affixed.
Figure 10:
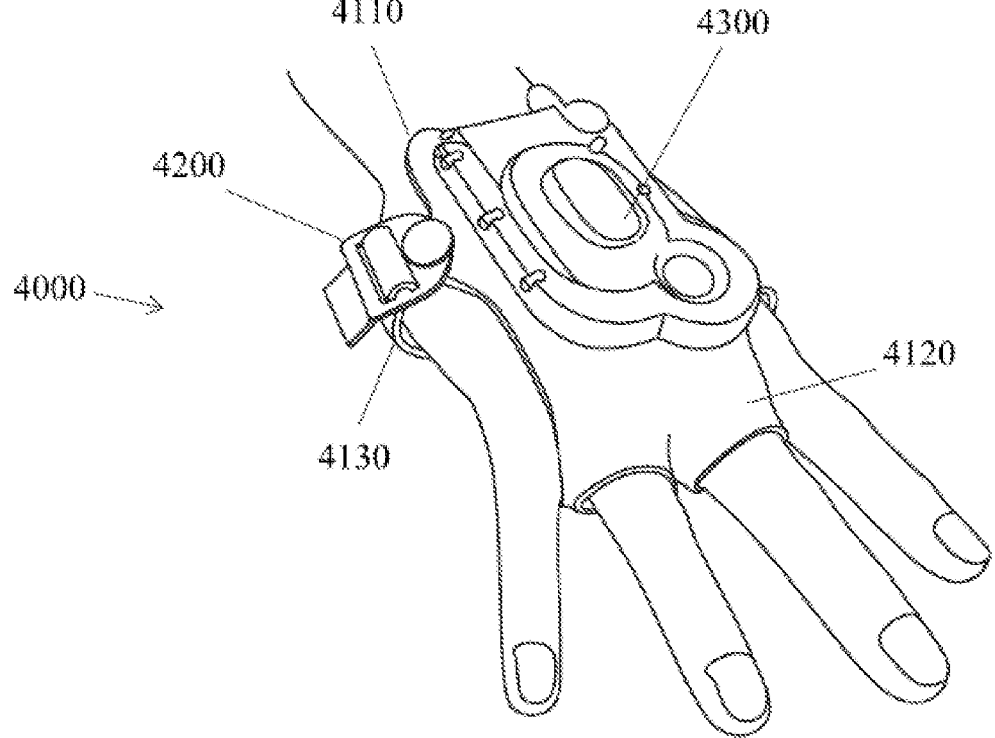
FIG. 10 is a side perspective view of the apparatus of FIG. 9, mounted on a user's hand ($5^{th}$ digit side).
Figure 11:
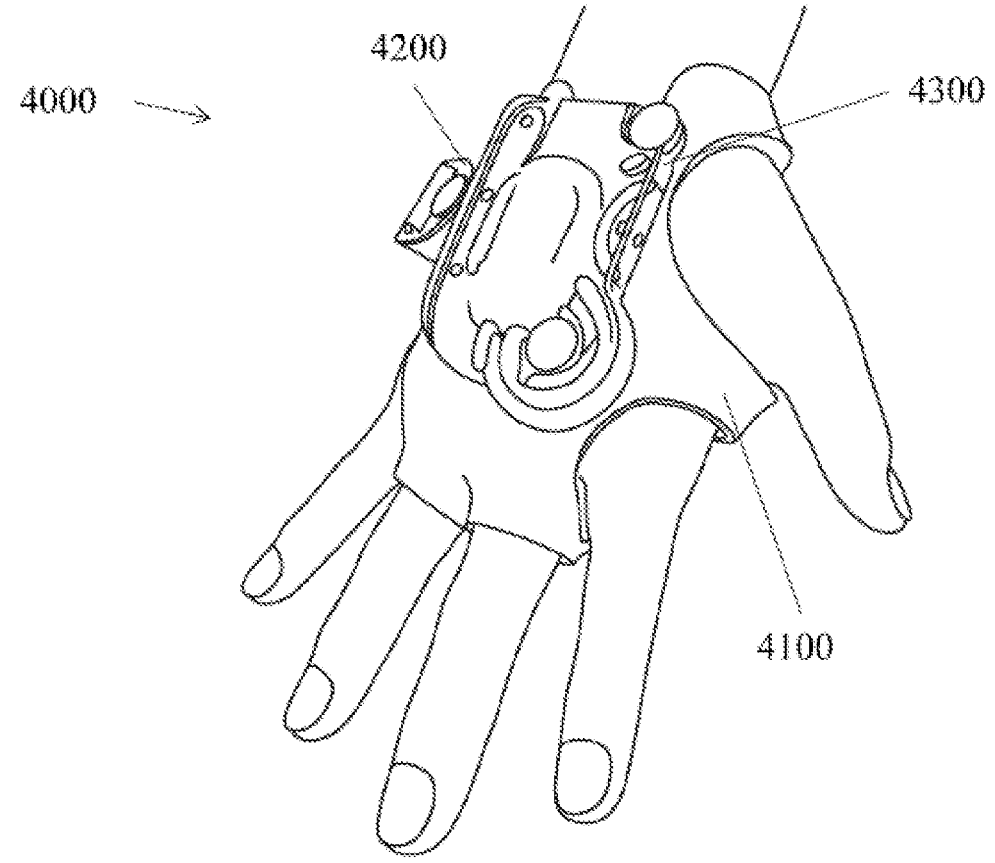
FIG. 11 is a side perspective view of the apparatus of FIG. 9, mounted on a user's hand (thumb side).
Figure 12:
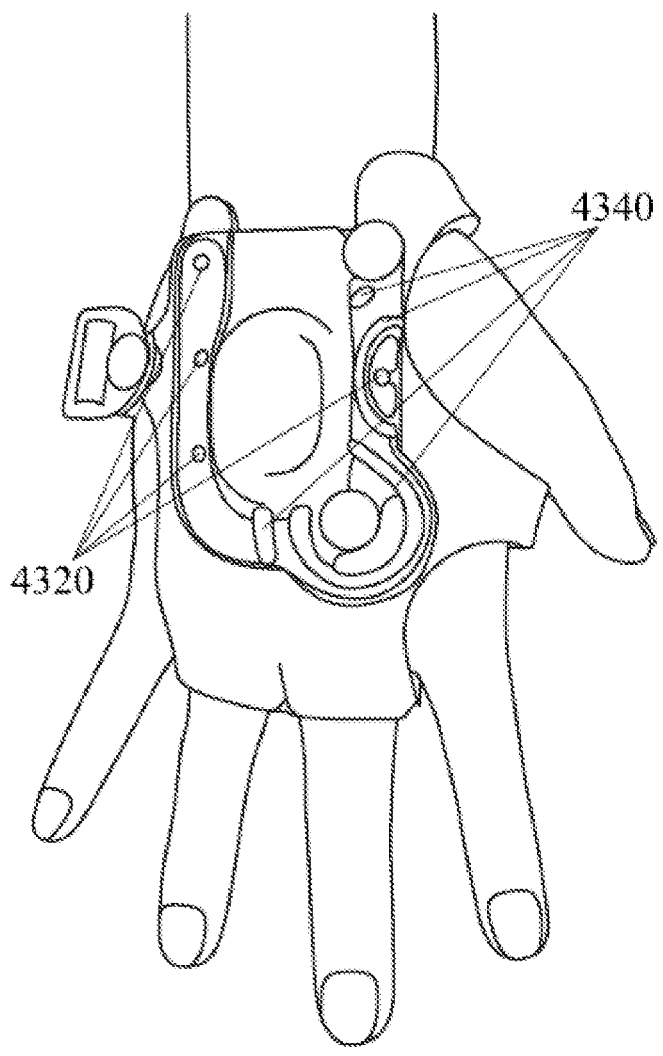
FIG. 12 is a top plan view of the apparatus of FIG. 9, mounted on a user's hand.
Figure 13:
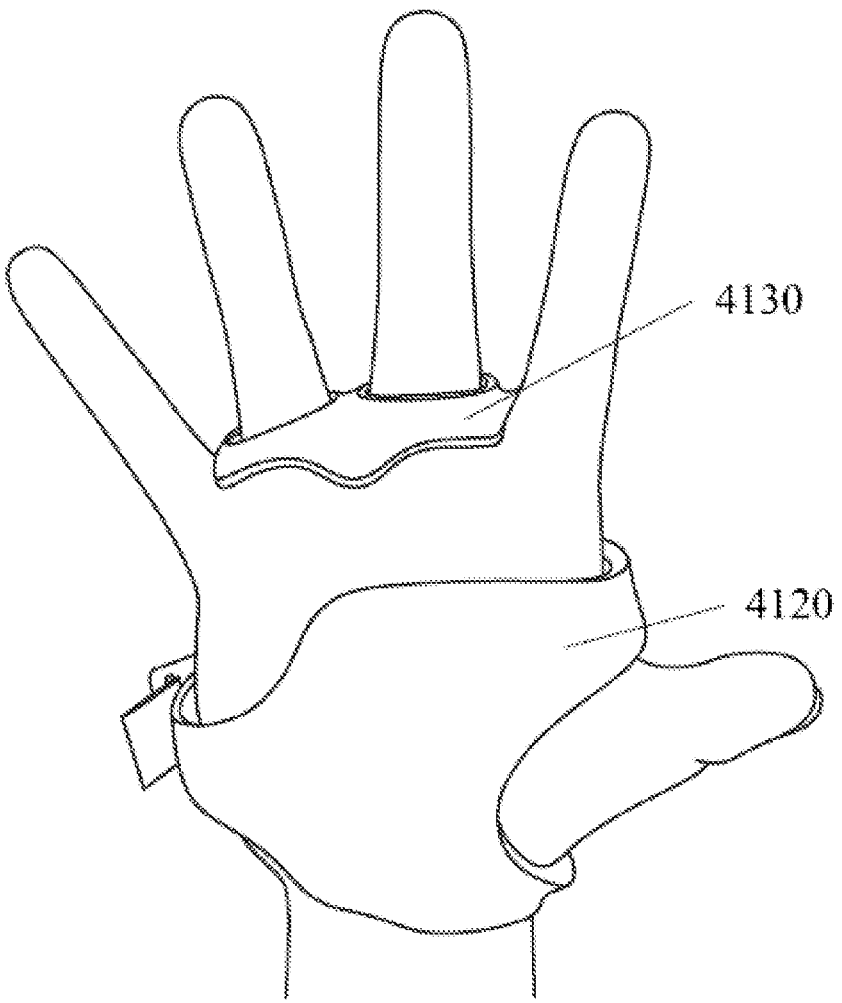
FIG. 13 is a bottom plan view of the apparatus of FIG. 9, mounted on a user's hand.

Apparatus 1000 is shown in FIGS. 7 and 8 as well. In FIGS. 7 and 8 apparatus 1000 is in an opened positioning in which the palm strap is released from ladder lock buckle 1200 and glove 1100 is spread out. As may be seen in FIGS. 7 and 8, glove 1100 is a glove blank on which buckle 1200 and housing 1300 are mounted to form apparatus 1000. Components of apparatus 1000 are designed for ease of manufacturing, transportation and storage, and use. Various materials may be used in the construction. For example, in some embodiments a housing, or elements of a housing, are made of plastic, such as moulded from a firm plastic. In some embodiments, a glove is a fabric glove, such as a fabric glove made of a microfiber or a scuba-like material such as a neoprene fabric.

A second embodiment is shown in FIGS. 9 to 13. Apparatus 4000 is shown on hand 2000 and holding intravenous line 3000. Apparatus 4000 includes a fabric glove 4100, a buckle 4200 and a housing 4300. The fabric glove 4100 is a continuous panel which is secured via buckle 4200 to itself around hand 2000. Glove 4100 of apparatus 4000 forms a mounting panel 4110, a palm strap 4120, and a pair of finger loops 4130. Mounting panel 4110 is provided to hold housing 4300, palm strap 4120 is provided to extend under the user's hand and join to the mounting panel 4110 via buckle 4200, and the forward finger loops 4130 are provided to fit over the fingers of a user.

Housing 4300 is provided to house the insertion point of an intravenous line. Housing 4300 is mounted on glove 4100 on a dorsal surface of hand 2000. Housing 4300 is designed to receive an intravenous line for insertion into the dorsal surface of hand 2000. Housing 4300 includes a footing 4310 secured to glove 4100 by a set of fasteners 4320. Housing 4300 also includes an upper cover 4330 secured to the footing 4310 by way of a combination of a friction overlay of footing 4310 and a set of fasteners 4350. Footing 4310 defines a set of clip projections 4340, together the set of clip projections 4340 define an intravenous line guide for holding an intravenous line. Fasteners may be held to panel 4110 in a variety of ways, such as via adhesive, mechanical clips, or hook-and-loop components.

Figure 14:
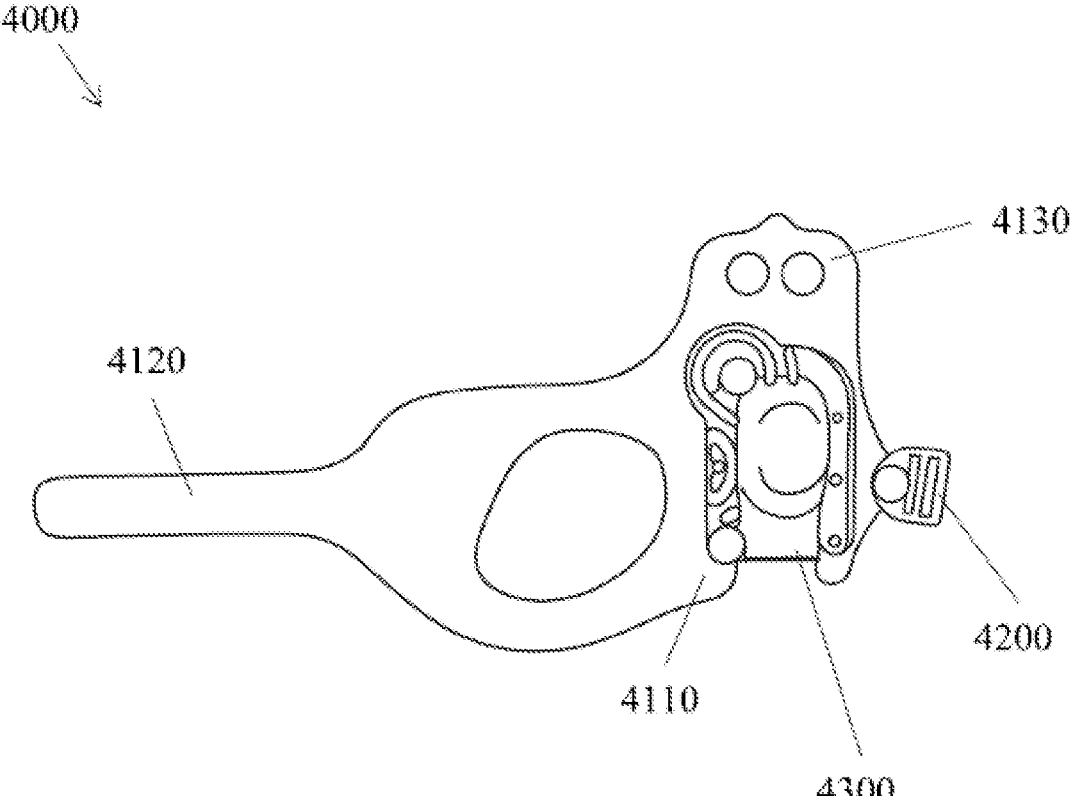
FIG. 14 is a top plan view of the apparatus of FIG. 9, opened and with an opaque cover affixed.

Cover 4330 may be clear or opaque; it is shown in FIGS. 9 to 12 and 16 as a clear cover and in FIG. 14 as an opaque cover. Cover 4330 may also be interchangeable, such as to allow a clear cover to be swapped for an opaque cover.

Figure 15:
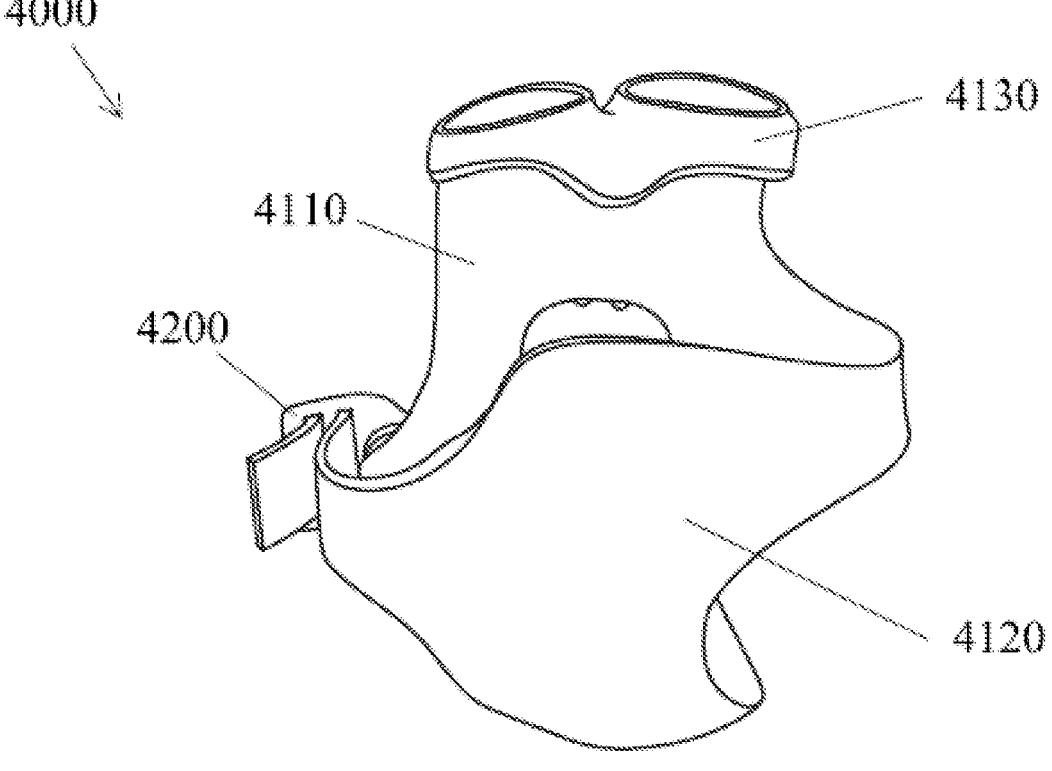
FIG. 15 is a bottom perspective view of the apparatus of FIG. 9, closed but unmounted.
Figure 16:
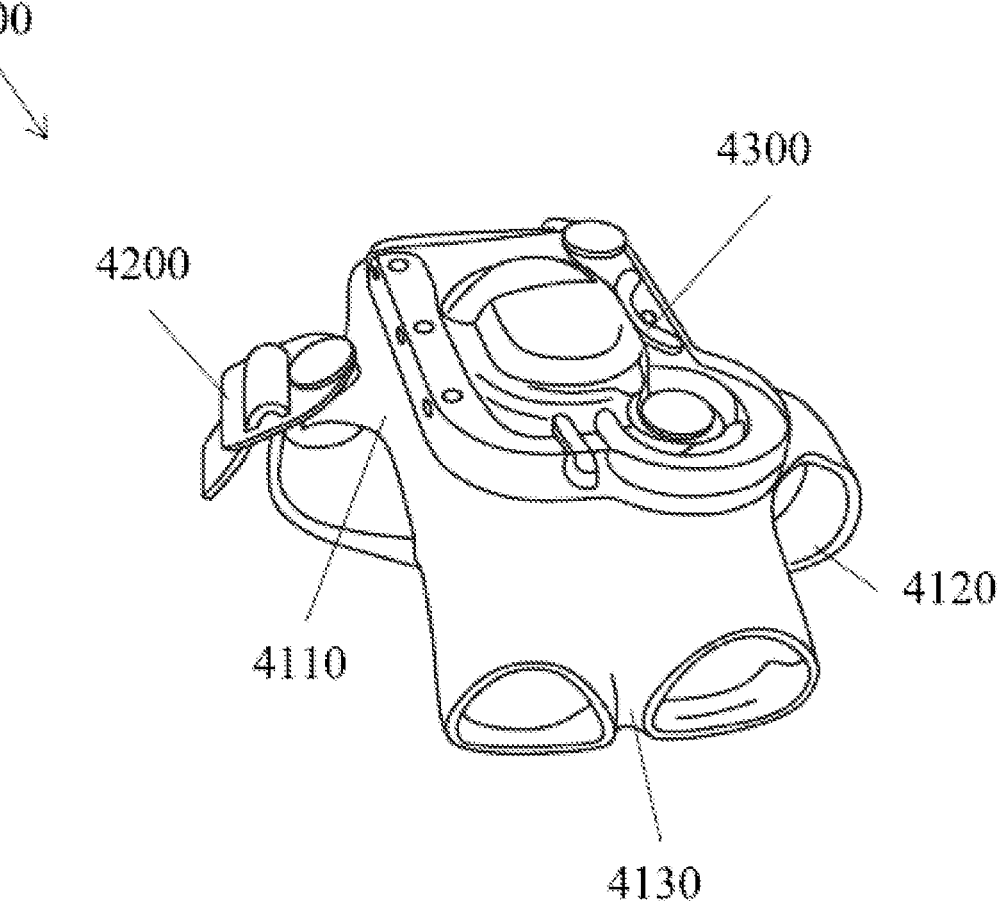
FIG. 16 is a top perspective view of the apparatus of FIG. 9, closed but unmounted and with a clear cover affixed.

Apparatus 4000 is also shown in FIGS. 14 to 16. In FIG. 14 apparatus 4000 is in an opened positioning in which the palm strap is released from ladder lock buckle 4200 and glove 4100 is spread out. In FIGS. 15 and 16 apparatus 4000 is in a closed positioning in which the palm strap is secured to ladder lock buckle 4200 but is empty of a user's hand.

Figures 17A, 17B, 17C:
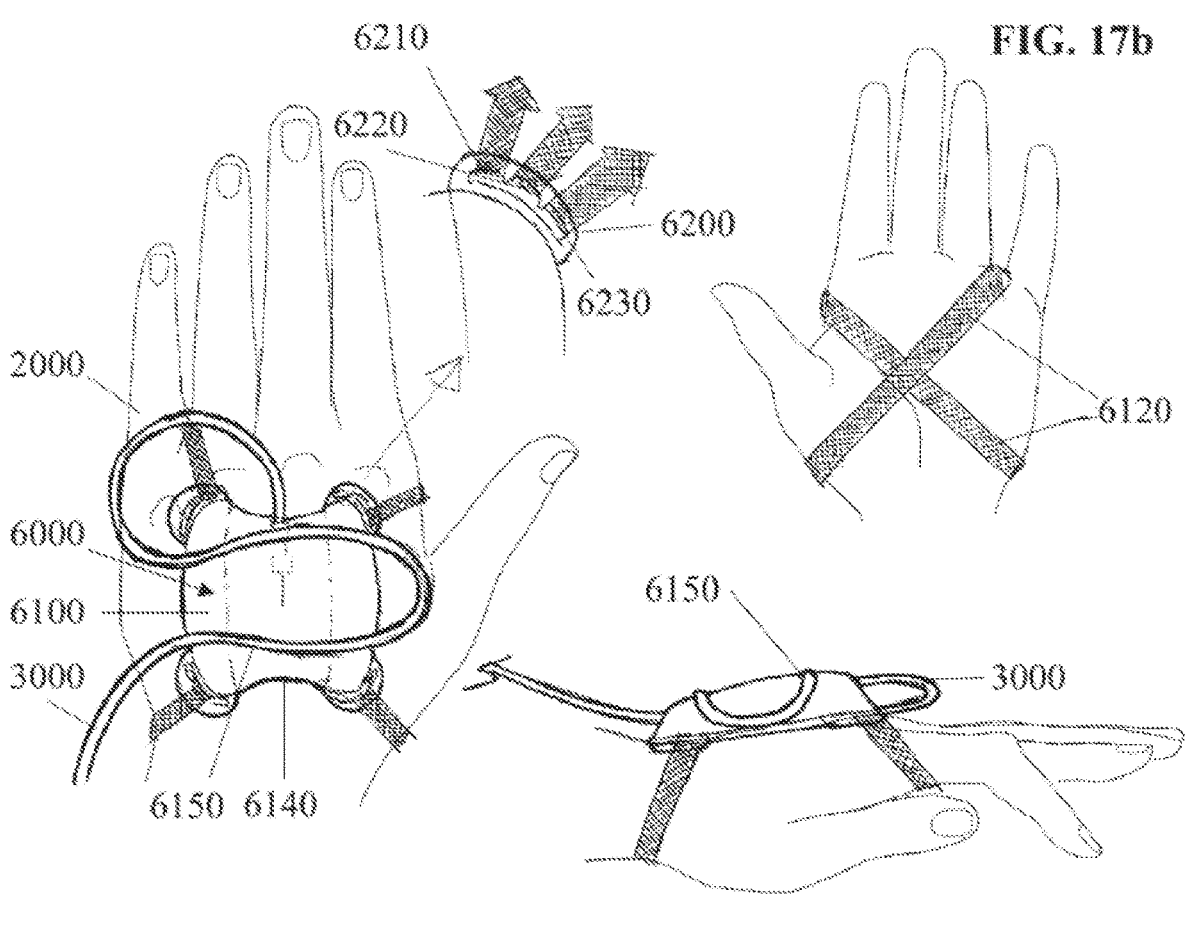
FIGS. 17a, 17b and 17c show an apparatus for holding an intravenous line according to an embodiment mounted on a user's hand and with an intravenous line affixed from a top plan view, bottom plan view and an elevational view (thumb side), respectively.

According to a third embodiment as shown in FIGS. 17*a*, 17*b* and 17*c*, an apparatus 6000 may comprise an intravenous line housing 6100 that includes a groove 6150 to hold an intravenous line 3000 by friction fit. The apparatus 6000 may be a glove configured to be suitable for wearing on both a right or left human hand 2000 comprising straps 6120 which may engage with the intravenous line housing 6100 via multi-way adjustable loops such as 3-way adjustable loop (or eyelet) 6200 which may include three different positions 6210, 6220 and 6230 for a strap to pass through. Once the strap 6120 is stretched into place, it may remain in the desired eyelet groove for the particular position. According to an embodiment, the intravenous housing 6100 may also be recessed adjacent the user's wrist for comfort as shown at 6140.

Figures 18A, 18B, 18C:
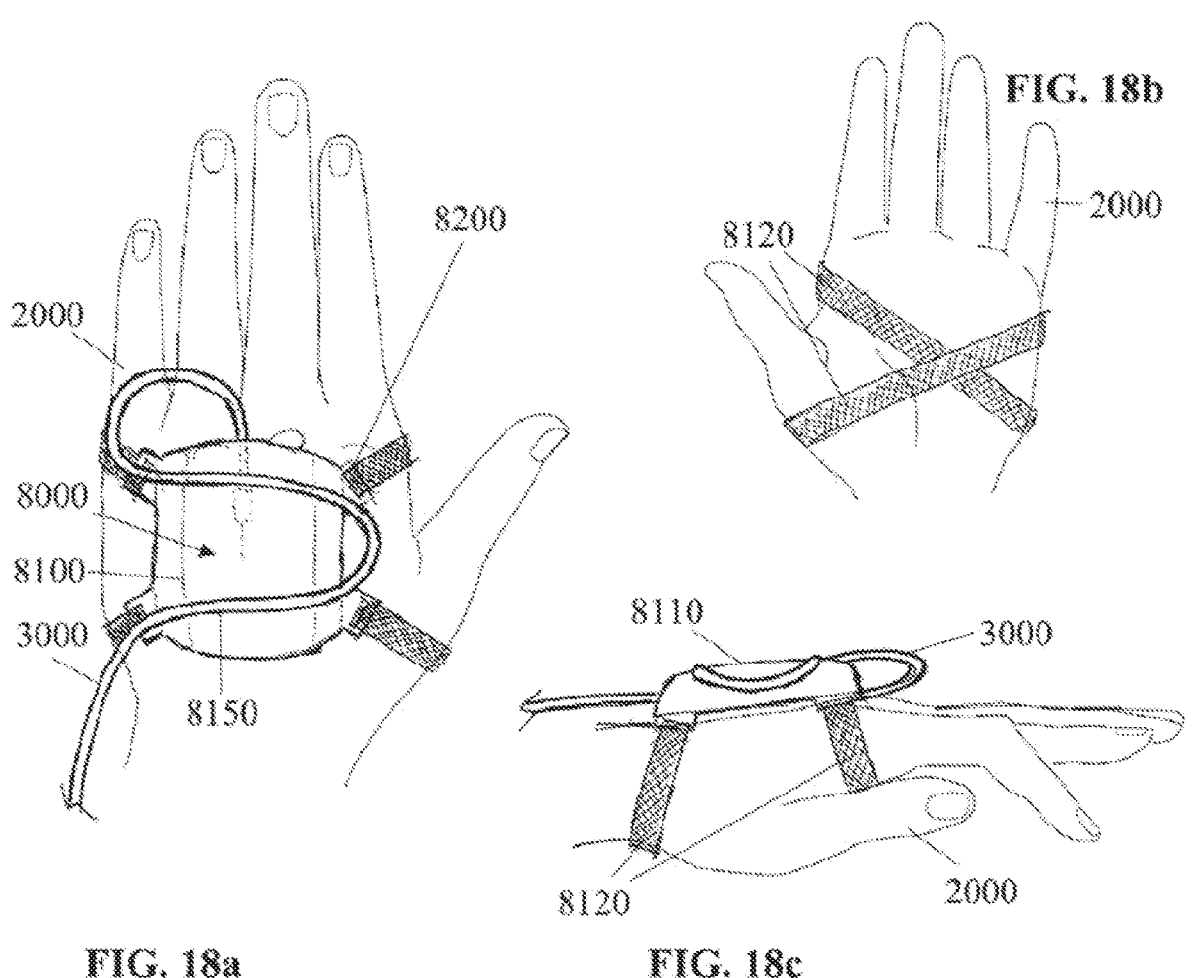
FIGS. 18a, 18b and 18c show an apparatus for holding an intravenous line according to an embodiment mounted on a user's hand and with an intravenous line affixed from a top plan view, bottom plan view and an elevational view (thumb side), respectively.
Figures 19A, 19B, 19C, 19D, 19E, 19F, 19G:
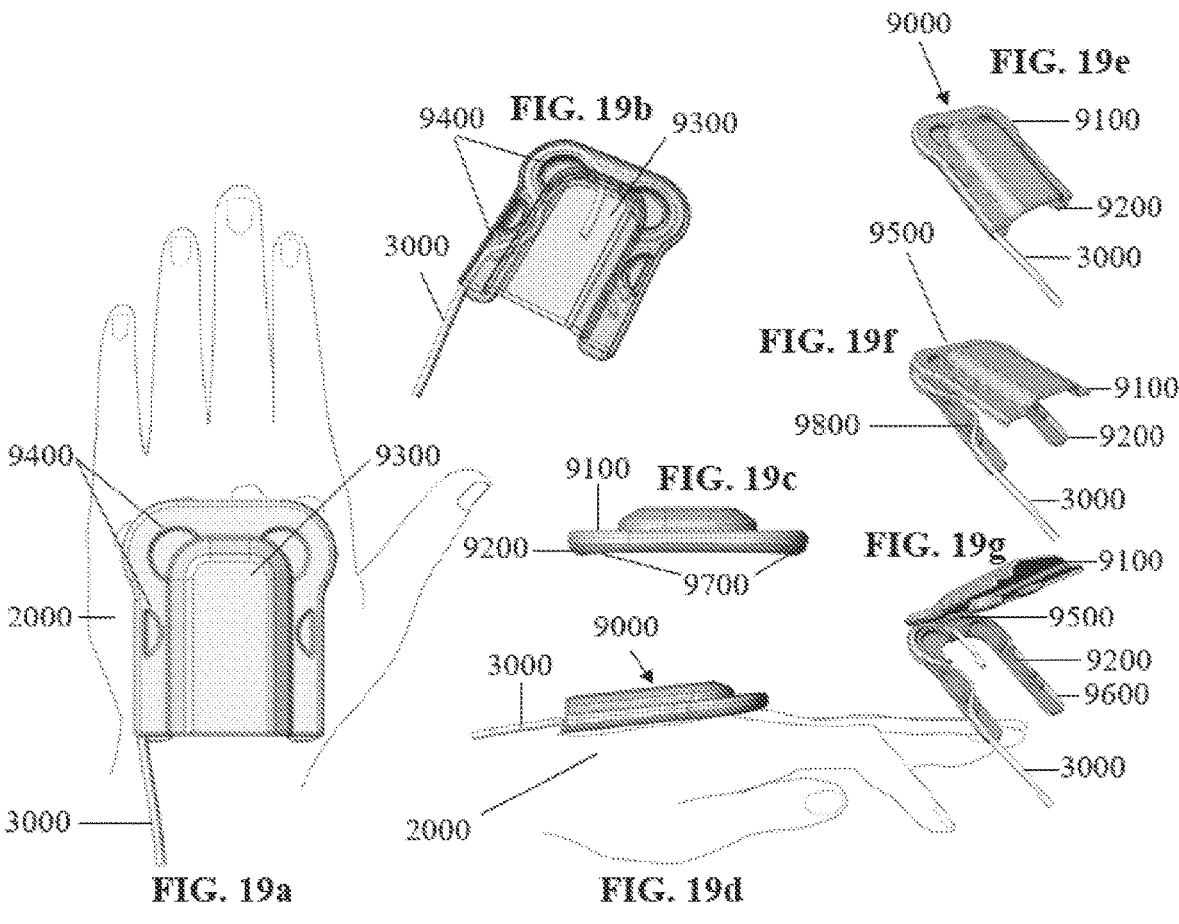
Figure 19H:
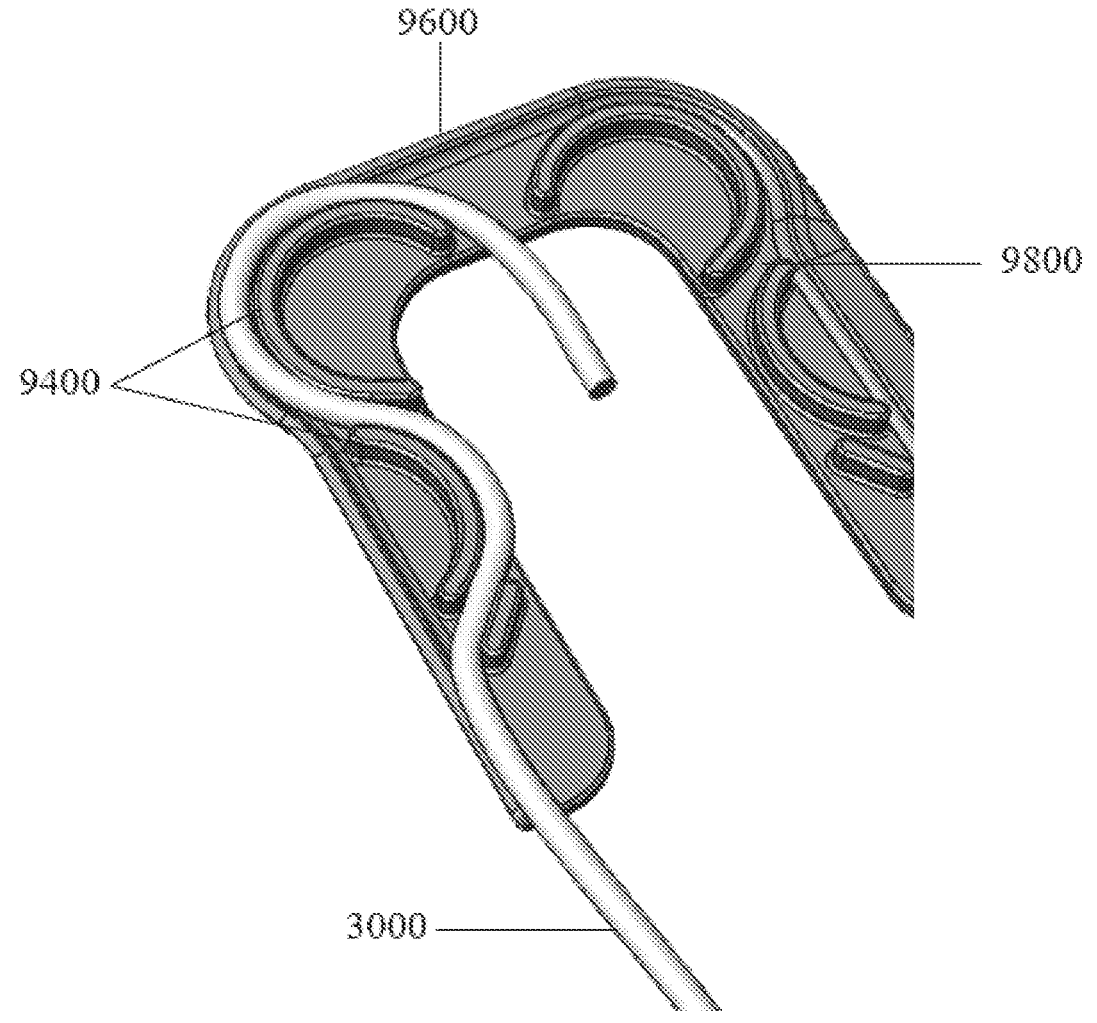
FIG. 19h is a top perspective view of the apparatus of FIG. 19a, removed from a user's hand and with an outer cover removed.

According to a fourth embodiment as shown in FIGS. 18*a*, 18*b* and 18*c*, an apparatus 8000 may comprise an intravenous line housing 8100 that includes a groove 8150 to hold an intravenous line 3000 by friction fit. The apparatus 8000 may be a glove configured to be suitable for wearing on both a right or left human hand 2000 and comprise straps 8120 which may engage with the intravenous line housing 8100 via loops (or eyelets) 8200 for the strap to pass through. Loops (or eyelets) 8200 may be proximate to the perimeter of the intravenous line housing 8100 as shown or elsewhere on the housing 8100 such that the straps 8120 serve to retain the intravenous line housing 8100 on the hand 2000. According to an embodiment, intravenous line housing may comprise a clear injection molded thin wall 8110. According to an embodiment, the intravenous line housing 8100 may have open ends meaning that the housing is not flush to the surface of the skin of a hand 2000 at either end. This may allow space for the intravenous catheter and line beneath the intravenous line housing 8100. According to an embodiment, the intravenous line housing 8100 may have a convex geometry which may allow better articulation of the wrist for extended use.

According to a fifth embodiment as shown in FIGS. 19*a* to 19*h*, an apparatus 9000 for housing an intravenous line 3000 may be a clamshell design, consisting of an outer cover 9100 that rotates about hinge 9500 to separate outer cover 9100 from base portion 9200. The outer cover 9100 may further comprise a transparent and raised inspection dome 9300 to allow for inspection and protection of an inserted intravenous line 3000. Apparatus 9000 may further include at least one snap fit mechanism to secure intravenous line 3000 between outer cover 9100 and base portion 9200 in a closed position. The at least one snap fit mechanism may be formed as a result of a male portion of outer cover 9100 coupling to a female portion of base portion 9200. Base portion 9200 may further include a raised perimeter 9600 and a series of complimentary raised edges 9400 and grooves 9800 in, for example, an s-shaped configuration to secure the intravenous line 3000 by friction fit to base portion 9200. Raised perimeter 9600 and raised edges 9400 and grooves 9800 are provided in a mirrored configuration on a right side and left side of apparatus 9000, to allow right-hand or a left-hand usage of apparatus 9000. The mirrored configuration also allows for insertion of an intravenous line 3000 at various positions underneath raised inspection dome 9300, as is displayed in FIG. 20. The base portion 9200 may have curvature 9700 to help provide a comfortable fit when in use.

Figure 20:
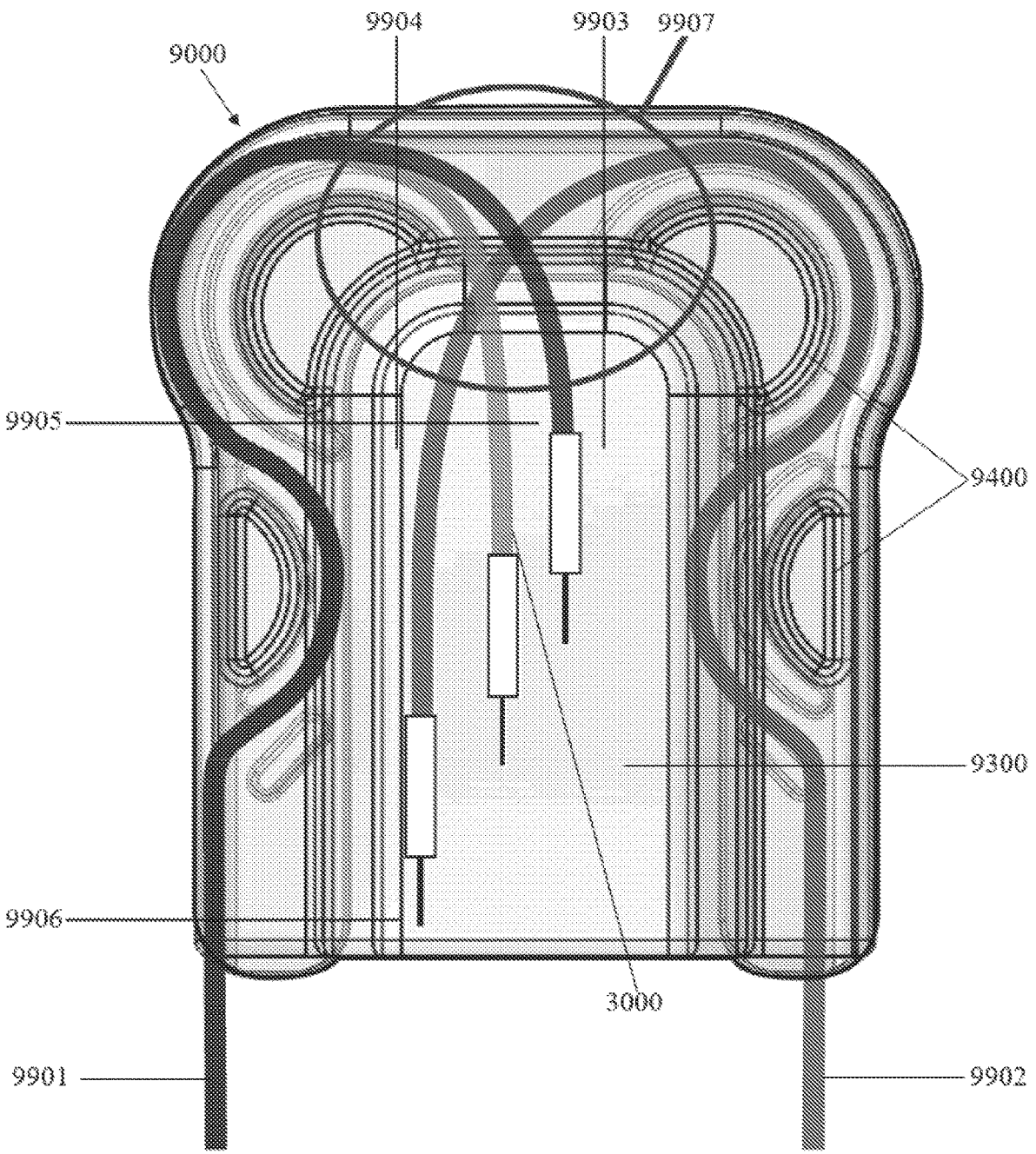
FIG. 20 is a top plan view of the apparatus of FIG. 19a, removed from a user's hand and with three intravenous lines situated in three different positions.

As shown in FIG. 20, at least one of intravenous lines 3000, 9901 or 9902 can be configured to terminate in a right 9903, left 9904, high 9905 or low 9906 position. A slack zone 9907 permits any of intravenous lines 3000, 9901 or 9902 to change between the right 9903, left 9904, high 9905 or low 9906 positions. Slack zone 9907 increases the range of insertion points for intravenous lines 3000, 9901 or 9902 and may increase comfort by reducing the tautness of intravenous lines 3000, 9901 or 9902. Further, apparatus 9000 may allow for securing up to three intravenous lines.

Figures 21A, 21B, 21C:
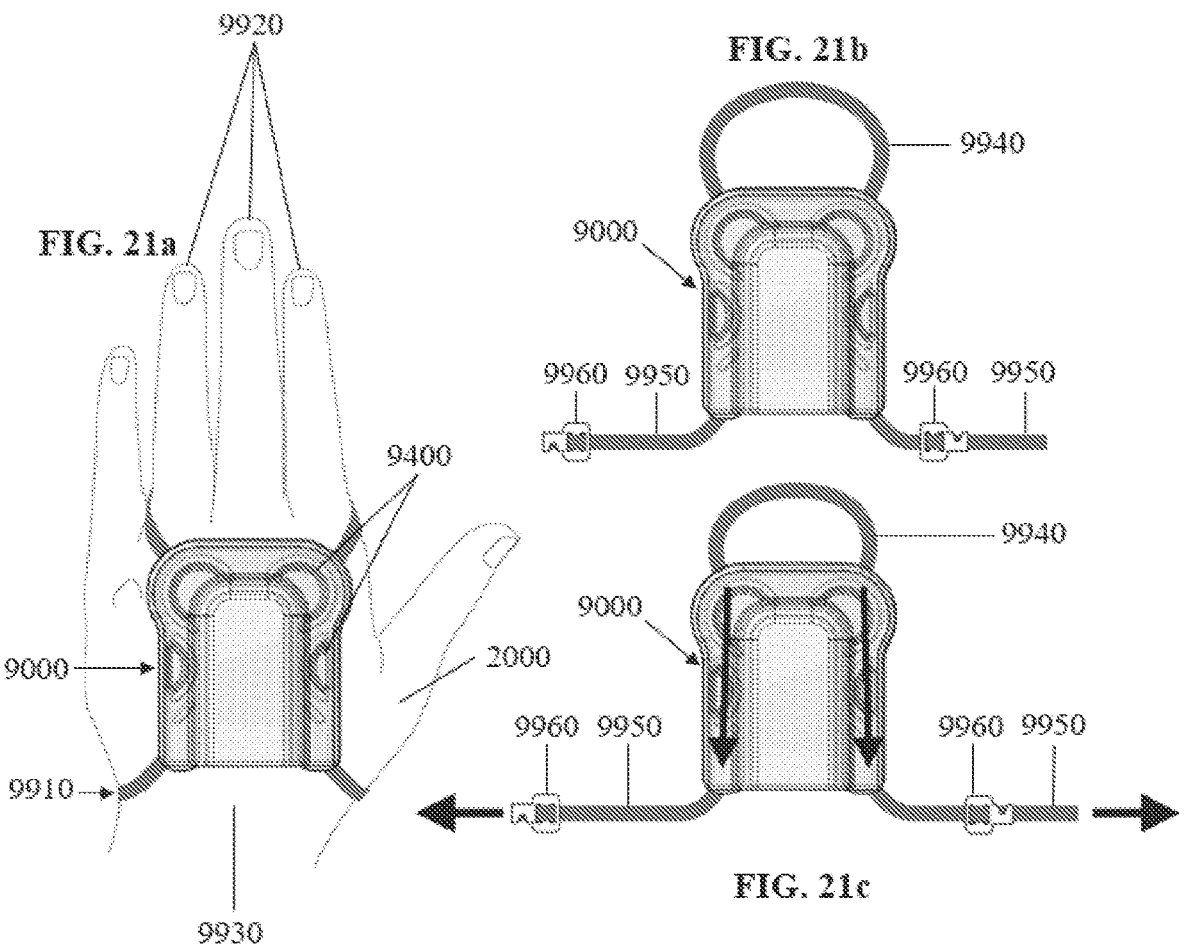
FIG. 21a is a top plan view of the apparatus of FIG. 19a, secured to a user's hand with a strap.
FIGS. 21b and 21c are top plan views of the apparatus of FIG. 21a, removed from a user's hand.

As shown in FIGS. 21*a*, 21*b* and 21*c*, strap 9910 interlaces with apparatus 9000 to secure apparatus 9000 around one or more fingers 9920 and a wrist 9930 of a hand 2000. Strap 9901 is comprised of a finger loop 9940 that can be fit around one or more fingers 9920 and terminal portions 9950 that may be wrapped around and secured about a wrist 9930. Terminal portions 9950 can be pulled to tighten the finger loop 9940 around one or more fingers 9920. Terminal portions 9950 are also fitted with at least two strap clips 9960 that are configured to couple and secure terminal portions 9950 around a wrist 9930.

Figure 22A:
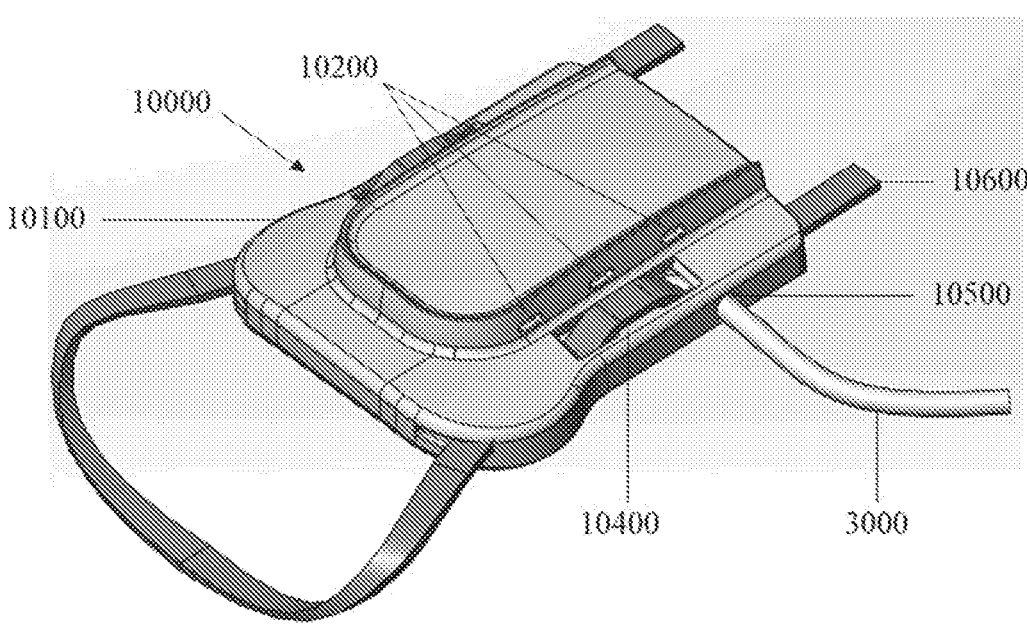
FIG. 22a is a top perspective view of an apparatus for holding an intravenous line according to an embodiment with a lateral intravenous line aperture, ventilation apertures, a splash guard, dorsal strap adjustment apertures, and with an intravenous line affixed.
Figure 22B:
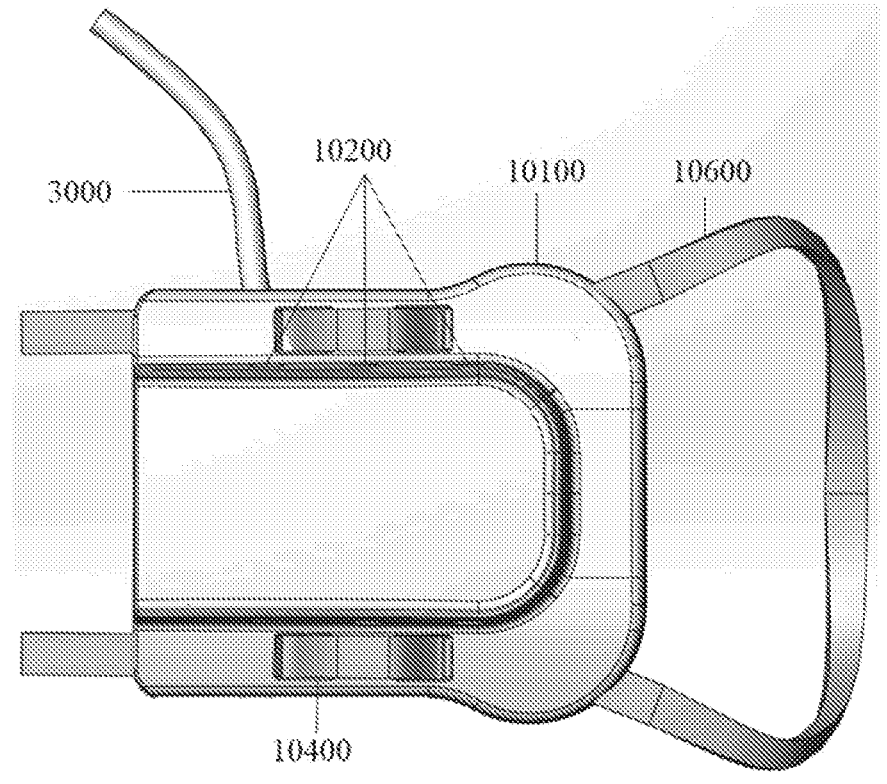
Figure 22C:
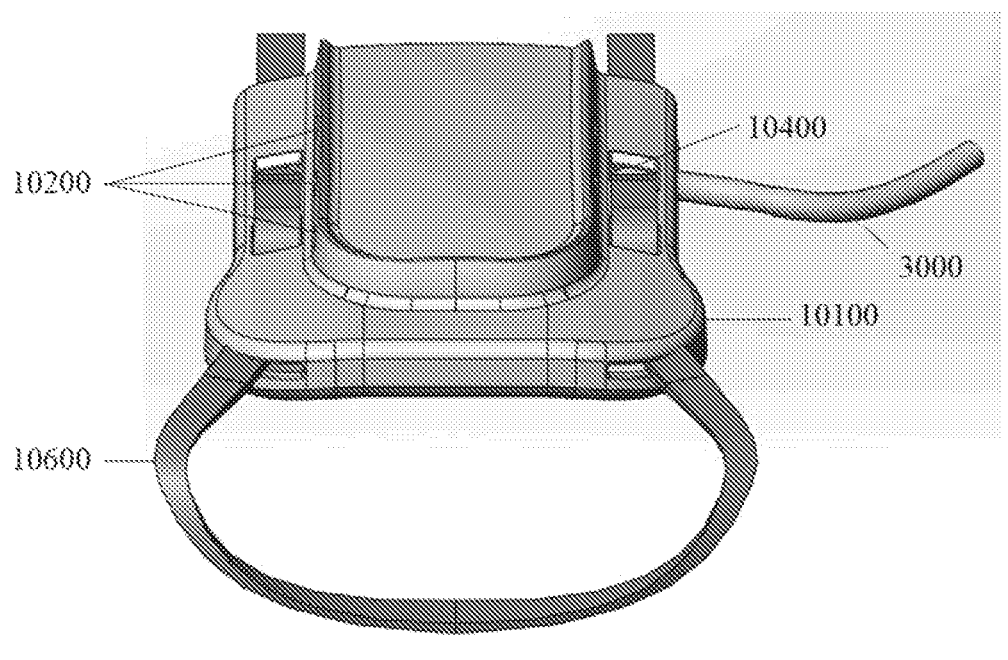
Figure 22D:
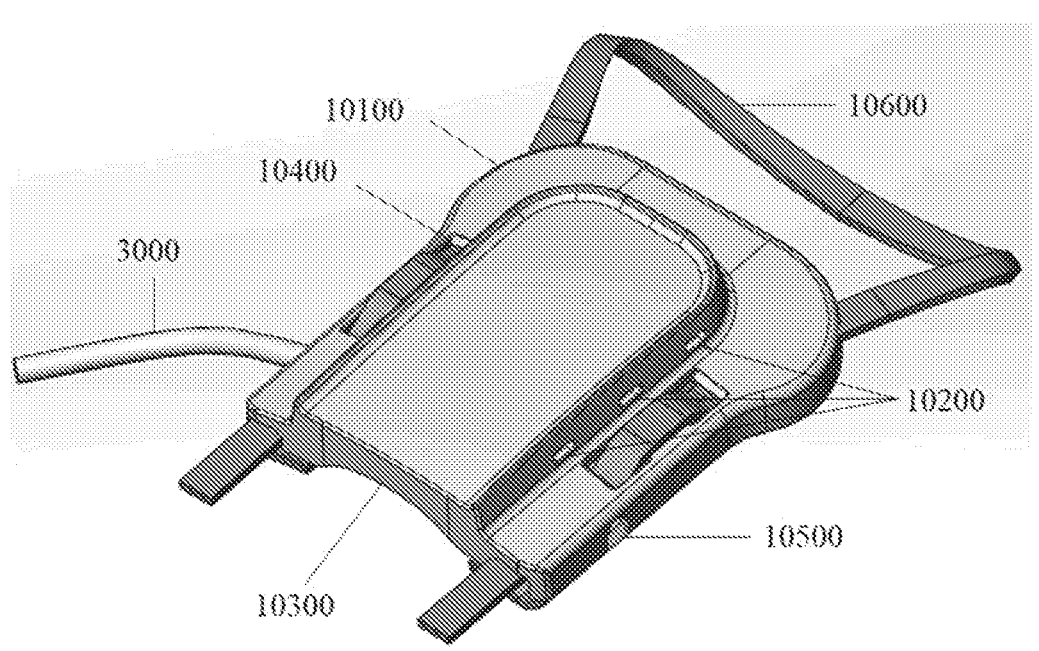
FIG. 22d is a rear perspective view of the apparatus of FIG. 22a wherein the rear splash guard is visible.
Figure 22E:
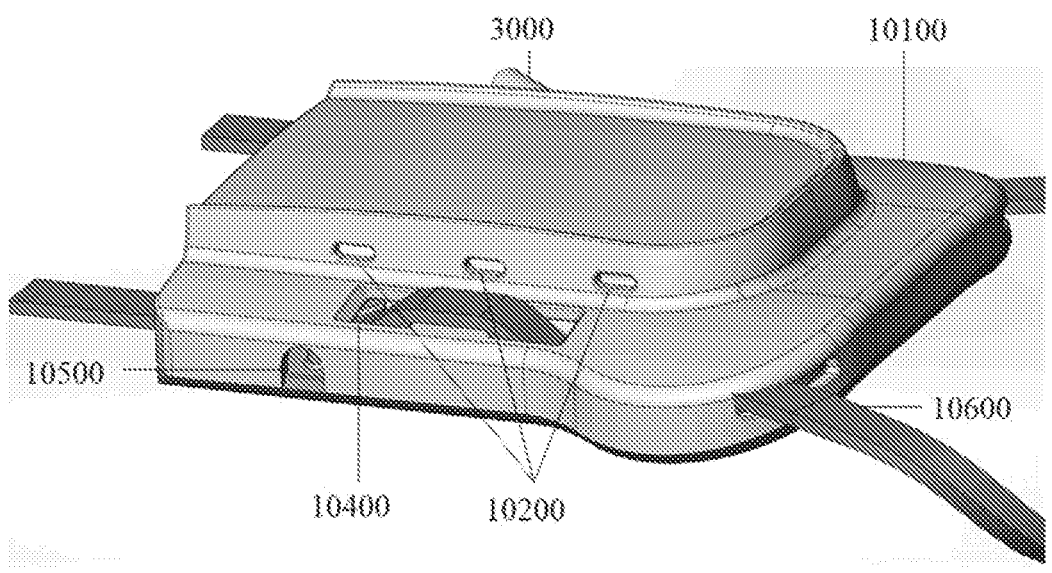
Figure 22F:
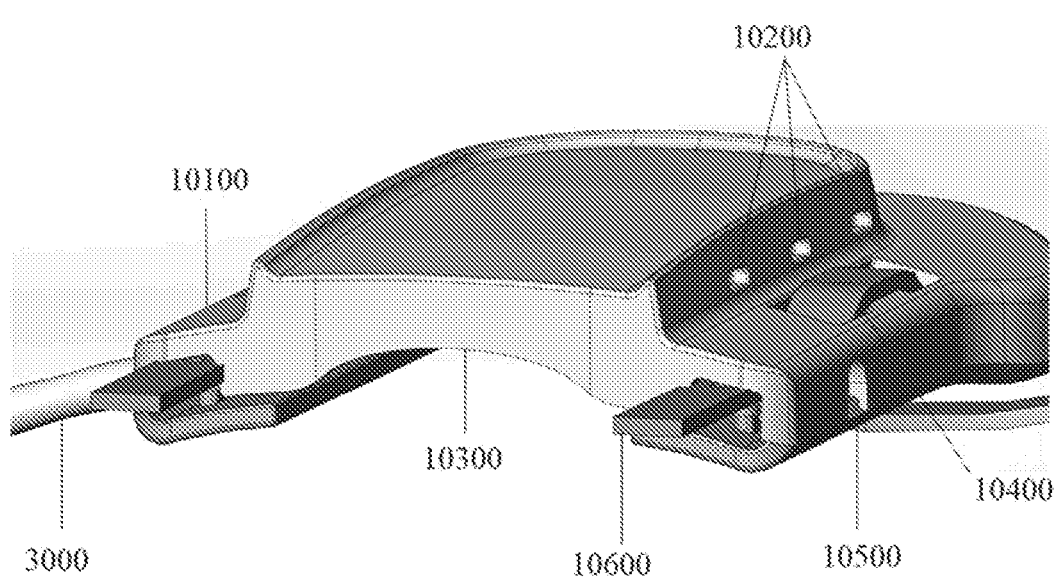
Figure 22G:
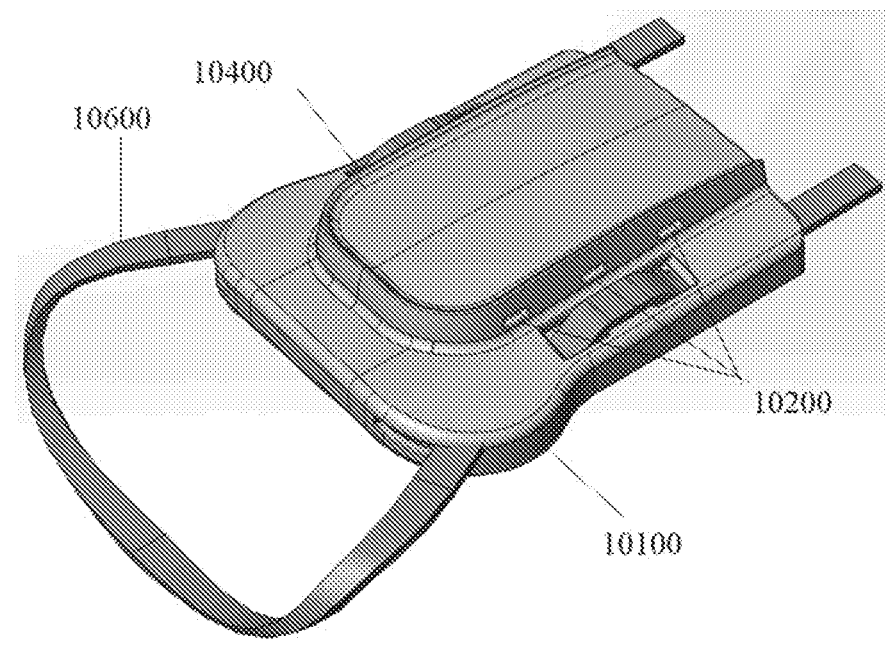
FIG. 22g is a top perspective view of the apparatus of FIG. 22a, without an intravenous line affixed.
Figure 22H:
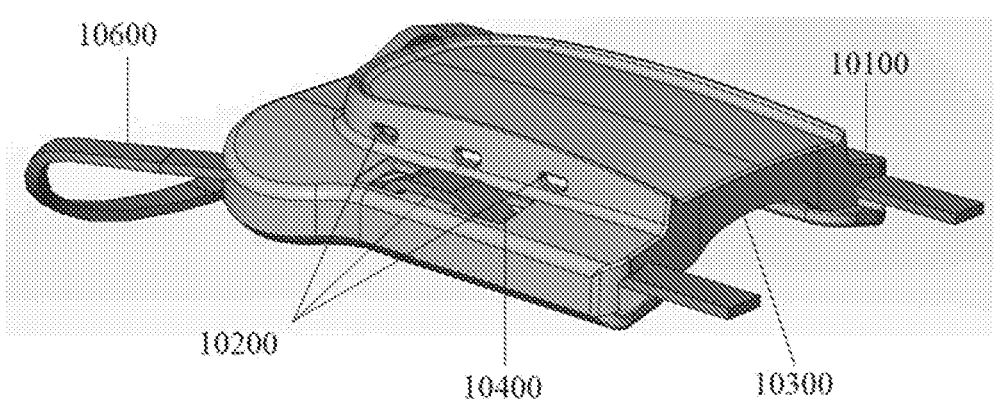
FIG. 22h is a rear perspective view of the apparatus of FIG. 22a, without an intravenous line affixed.
Figure 22I:
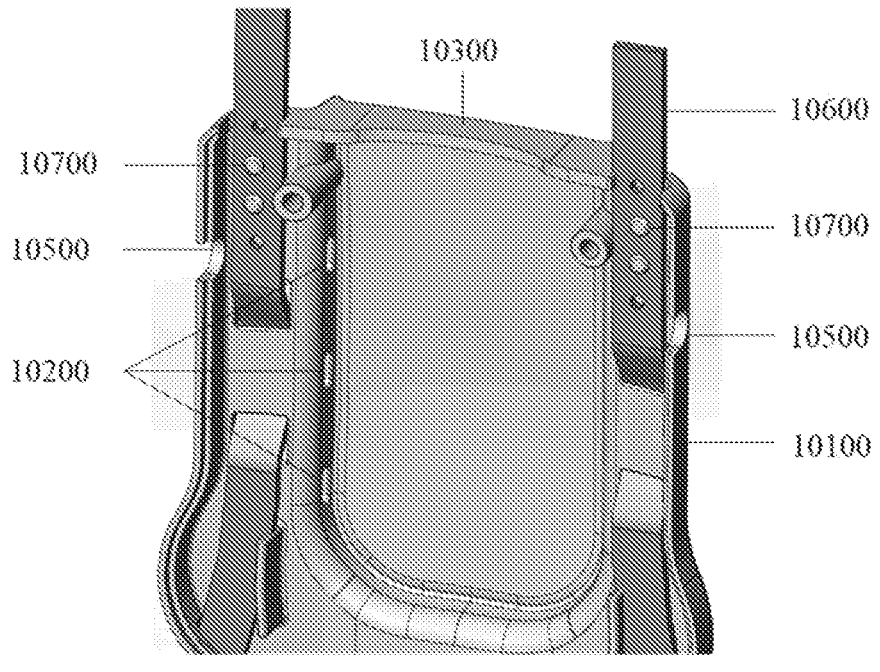
FIG. 22i is an internal view of the apparatus of FIG. 22a showing a pin and aperture-based strap securing mechanism that is visible when the apparatus is in an open configuration.
Figure 22J:
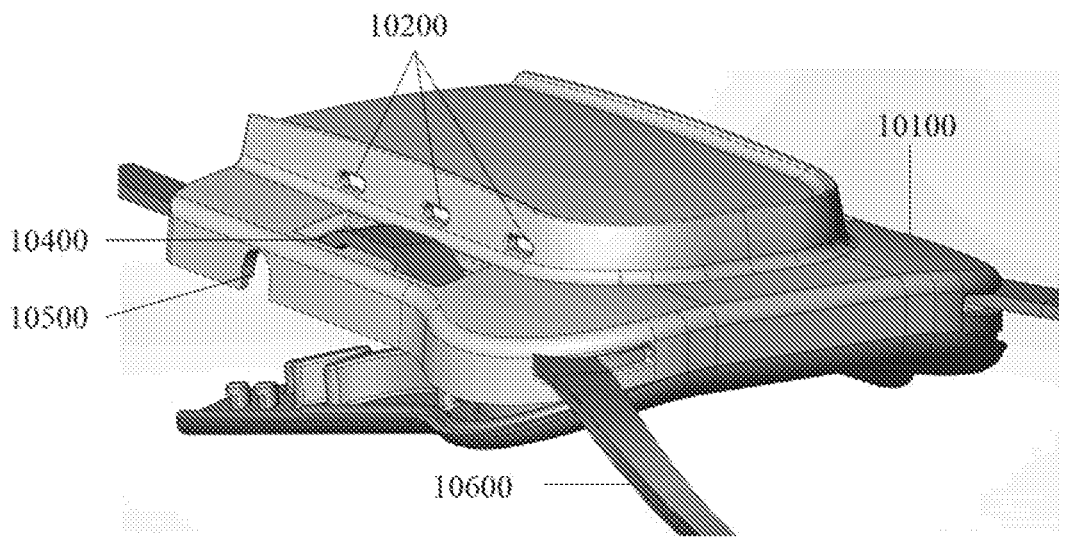
FIG. 22*j* is a front perspective view of the apparatus of FIG. 22*a* showing an outer cover rotating about a hinge to separate the outer cover from a footing.
Figure 22K:
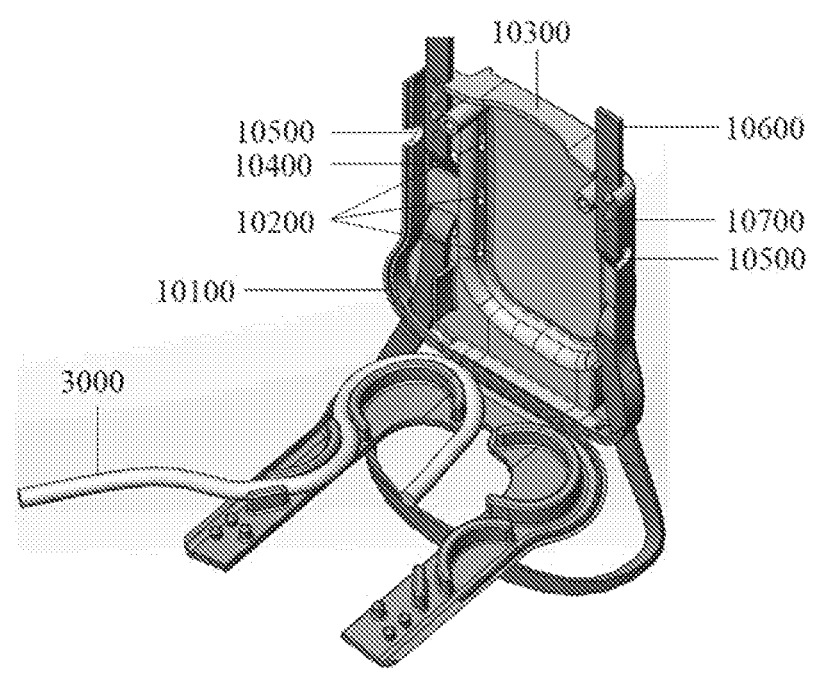
FIG. 22*k* is an internal view of the apparatus of FIG. 22*a* in an open configuration.
Figure 22L:
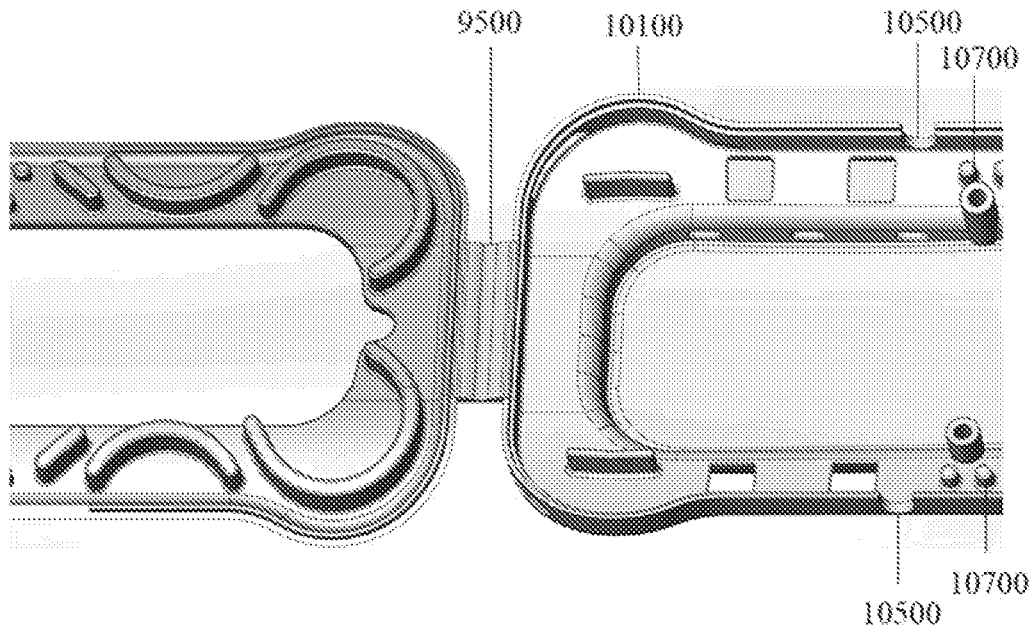
FIG. 22*l* is an internal close-up view of the apparatus of FIG. 22*a* in an open configuration, showing the outer cover, footing and hinge, without an intravenous line affixed.
Figure 22M:
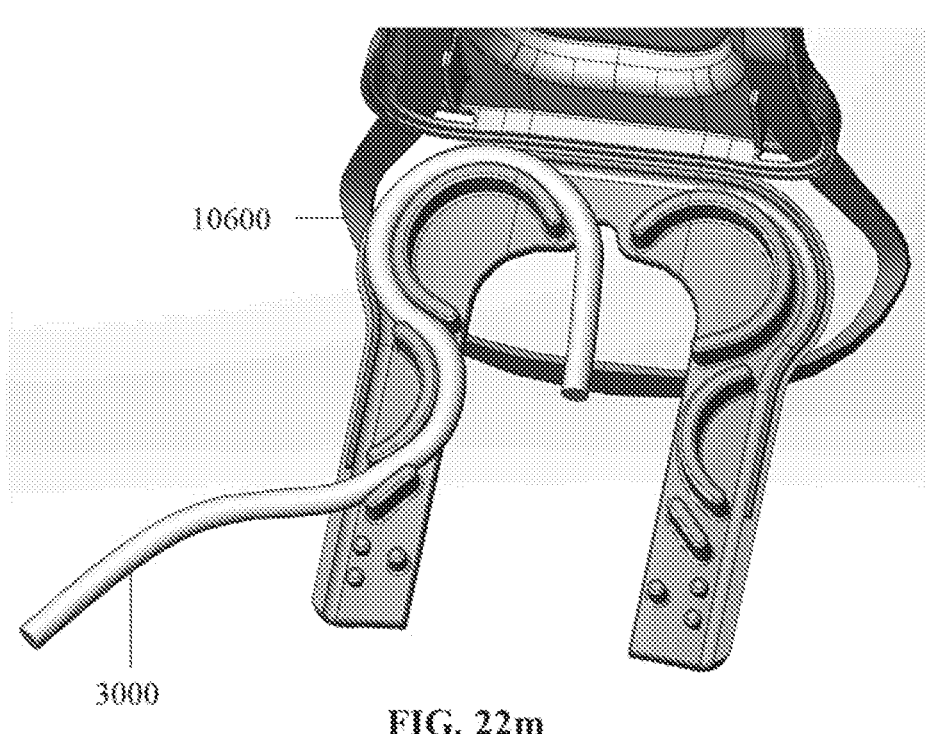
FIG. 22*m* is an internal close-up view of FIG. 22*a* showing in an open configuration showing the footing.

According to a sixth embodiment shown in FIGS. 22*a* to 22*m*, an apparatus 10000 for housing an intravenous line 3000 may consist of at least one lateral intravenous line aperture 10500 on the outer cover 10100 that permits an intravenous line 3000 to enter the apparatus from either the right or left lateral side. At least one ventilation aperture 10200 may be featured on the outer cover 10100 to permit free airflow between the inside and outside of the apparatus and help prevent the buildup of moisture. A splash guard 10300 may be featured on the outer cover 10100 to help prevent fluid leaks. Dorsal strap adjustment apertures 10400 can help permit easy access to a strap, such as strap 10600, so that its fit on a hand can be adjusted into a more comfortable and secure configuration. Comfort padding may also be included on any part of either the outer cover or the base portion according to any of the intravenous line holder embodiments disclosed herein. According to an embodiment shown in FIGS. 22*i*, 22*k* and 22*l*, the straps 10600 may feature a fastening mechanism 10700 that helps adjust and secure the configuration of the straps 10600 to the outer cover 10100. As shown in the figures, this fastening mechanism may utilize a snap fit configuration in which a male component couples with a female component.

Figure 23A:
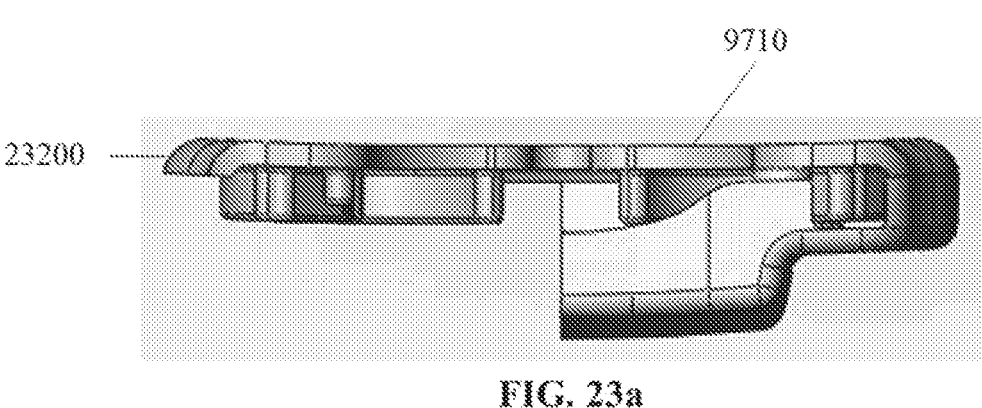
FIGS. 23*a* and 23*b* show cross-sectional views of an apparatus for holding an intravenous line with different footing curvatures.
Figure 23B:
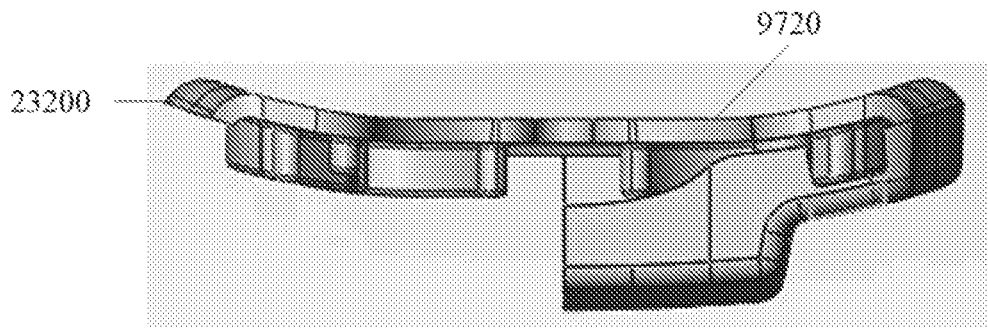

According to an embodiment of the intravenous line holder, as shown in FIGS. 23*a* and 23*b*, a base portion, such as base portion 23200, can either be configured with a shallow curvature 9710, a deeper curvature 9720, or any other curved or concave configuration that may help provide a comfortable and secure fit on a dorsal side of a user's hand.

Figure 24:
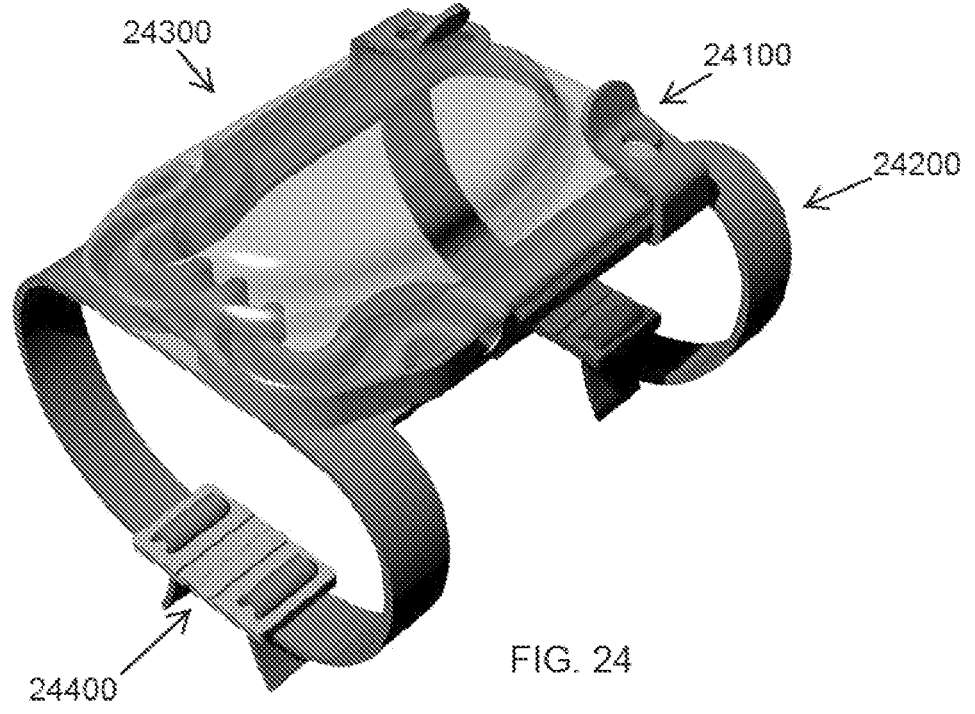
FIG. 24 shows a perspective view of an apparatus of an embodiment. with an intravenous affixed.

A further embodiment of the apparatus of the invention is shown in FIG. 24. In this embodiment, the apparatus comprises the intravenous line holder mounted on a generally U shaped base of the securing means. The securing means further comprises straps 24200 extending from the generally U shaped base in such a manner to allow the straps to wrap around the body part (such as an hand, arm or leg) the apparatus is to be attached to. The straps are adjustable and may comprise fastening mechanism 24400 that may utilize a snap fit configuration in which a male component couples with a female component. The securing means is constructed from flexible material such as a flexible plastic, neoprene etc. In this embodiment, a transparent cover 24300 is affixed to the intravenous line holder and secured to the apparatus by means of a fastening mechanism 24100. In certain embodiments, the fastening mechanism is one or more clips which may optionally be configured to include a male and female component.

Figure 25:
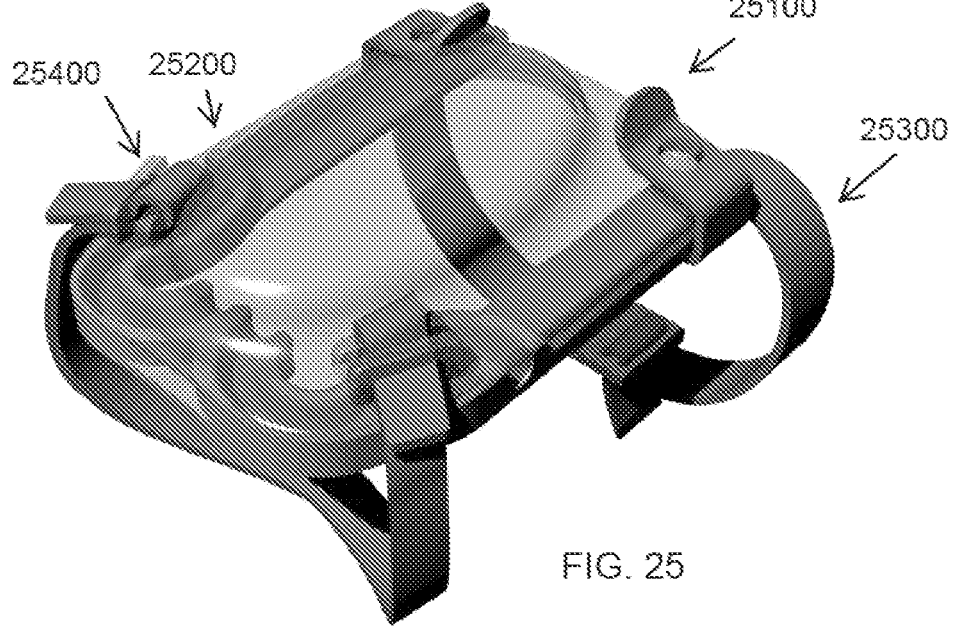
FIG. 25 shows a perspective of an apparatus of an embodiment.

A further embodiment of the apparatus of the invention is shown in FIG. 25. In this embodiment, the apparatus comprises the intravenous line holder mounted on a generally U shaped base of the a securing means. The securing means further comprises straps 25300 extending from the generally U shaped base in such a manner to allow the straps to wrap around the body part (such as an hand, arm or leg) the apparatus is to be attached to. In this embodiment, straps are also attached to the intravenous line holder. The straps are adjustable and may comprise fastening mechanism 24400 that may utilize a snap fit configuration in which a male component couples with a female component. The securing means is constructed from flexible material such as a flexible plastic, neoprene etc. In this embodiment, a transparent cover 25200 is affixed to the intravenous line holder and secured to the apparatus by means of a fastening mechanism 25100. In certain embodiments, the fastening mechanism is one or more clips which may optionally be configured to include a male and female component. In certain embodiments, the cover comprises openings 25400 to allow the straps attached to the intravenous line holder to pass through the cover. This allows for the straps to be adjusted without removing the cover.

Figure 26:
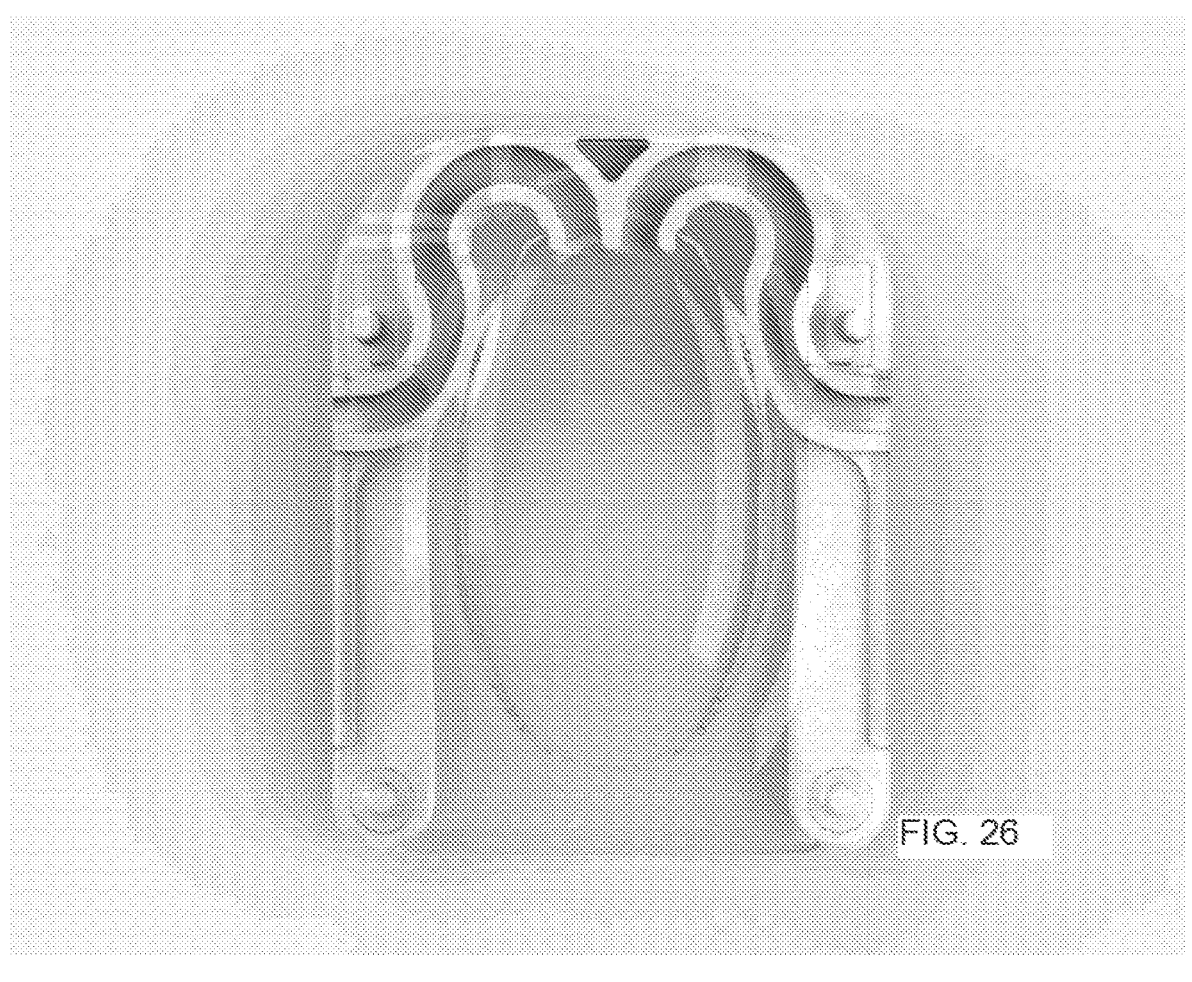
FIG. 26 shows a top view of an apparatus of an embodiment.
Figure 27:
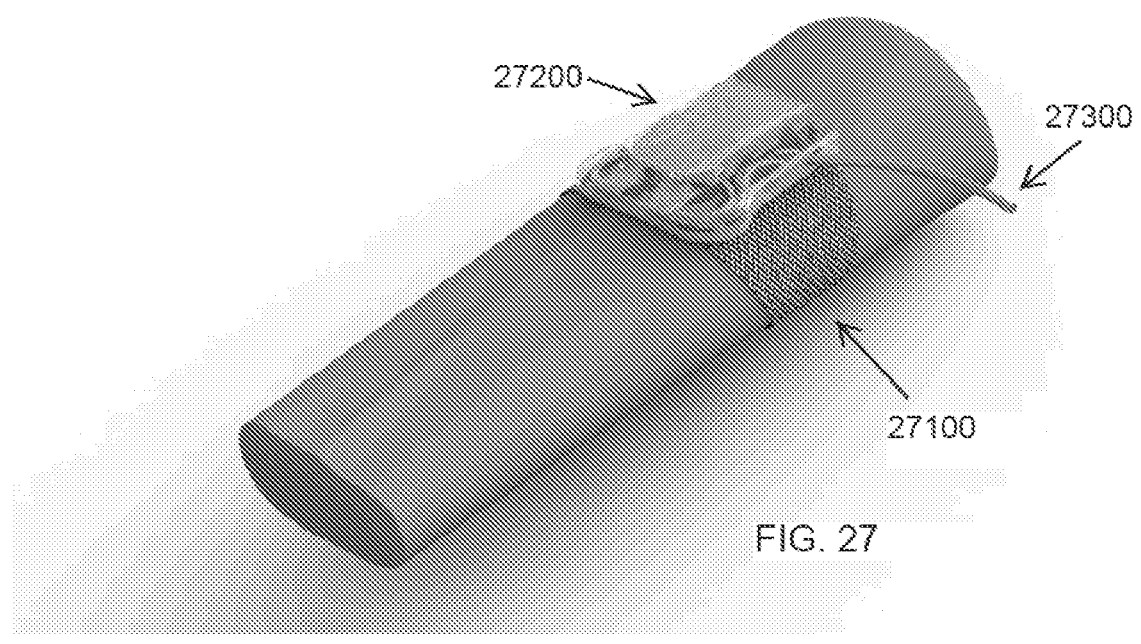
FIG. 27 shows an apparatus of an embodiment mounted on a limb (arm or leg).

A further embodiment of the intravenous line holder with cover attached is shown in FIG. 26. In this embodiment, the intravenous line holder comprises an s-shaped groove and an inverse s-shaped groove for the intravenous line. In this embodiment, the holder comprises pegs which correspond to openings in the cover to ensure that the cover stays in position. A further embodiment of the apparatus of the invention with intravenous line (27300) is shown in FIG. 27. In this embodiment, the intravenous line holder is mounted on a sleeve (27100) or band with closures and is covered with a clear cover (27200). In this embodiment, the intravenous line holder comprises an s-shaped groove and an inverse s-shaped groove for the intravenous line.

Various embodiments of the invention have been described in detail. Since changes in and or additions to the above-described best mode may be made without departing from the nature, spirit or scope of the invention, the invention is not to be limited to those details but only by the appended claims.

What is claimed is:

1. An apparatus, comprising:
    an intravenous line housing including a U-shaped base and a cover; and
    an intravenous line holder mounted on the U-shaped base, the intravenous line holder comprising a s-shaped groove and an inverse s-shaped groove, wherein the s-shaped groove and the inverse s-shaped groove are each configured to hold an intravenous line and direct the intravenous line towards entry into a patient.

2. The apparatus of claim 1, in which the intravenous line housing is adapted to be secured to the patient.

3. The apparatus of claim 2, in which the intravenous line housing is adapted to be secured to the patient via a glove disposed to be worn by the patient.

4. The apparatus of claim 2, in which the intravenous line housing is adapted to be secured to the patient via a flexible strap disposed to be worn by the patient.

5. The apparatus of claim 2, in which the intravenous line housing is adapted to be secured to the patient via a sleeve disposed to be worn by the patient.

* * * * *